United States Patent
Ibrahim et al.

(10) Patent No.: US 11,065,250 B2
(45) Date of Patent: Jul. 20, 2021

(54) SOLID DOSAGE FORMS OF PALBOCICLIB

(71) Applicant: PFIZER INC., New York, NY (US)

(72) Inventors: Fady Makram Louiz Ibrahim, East Lyme, CT (US); Matthew Patrick Mullarney, Niantic, CT (US); Ravi M. Shanker, Stonington, CT (US); Barbara Rodriguez Spong, Haddam, CT (US); Jian Wang, Killingworth, CT (US)

(73) Assignee: Pfizer Inc., New York, NY (US)

( * ) Notice: Subject to any disclaimer, the term of this patent is extended or adjusted under 35 U.S.C. 154(b) by 87 days.

(21) Appl. No.: 15/578,410

(22) PCT Filed: May 24, 2016

(86) PCT No.: PCT/IB2016/053040
§ 371 (c)(1),
(2) Date: Nov. 30, 2017

(87) PCT Pub. No.: WO2016/193860
PCT Pub. Date: Dec. 8, 2016

(65) Prior Publication Data
US 2018/0207100 A1    Jul. 26, 2018

Related U.S. Application Data

(60) Provisional application No. 62/171,177, filed on Jun. 4, 2015, provisional application No. 62/332,973, filed on May 6, 2016.

(51) Int. Cl.
*A61K 31/519* (2006.01)
*A61K 9/20* (2006.01)
(Continued)

(52) U.S. Cl.
CPC ............ *A61K 31/519* (2013.01); *A61K 9/205* (2013.01); *A61K 9/2009* (2013.01);
(Continued)

(58) Field of Classification Search
None
See application file for complete search history.

(56) References Cited

U.S. PATENT DOCUMENTS

| 6,936,612 B2 | 8/2005 | Barvian et al. |
| 7,208,489 B2 | 4/2007 | Barvian et al. |

(Continued)

FOREIGN PATENT DOCUMENTS

| EP | 2579855 | 3/2014 |
| EP | 2958916 | 9/2018 |

(Continued)

OTHER PUBLICATIONS

IBRANCE(R), Full Prescribing Information, Reference ID 3696527 (Feb. 2015). (Year: 2015).*

(Continued)

*Primary Examiner* — Bethany P Barham
*Assistant Examiner* — Barbara S Frazier
(74) *Attorney, Agent, or Firm* — Leslie A. Robinson

(57) ABSTRACT

The present invention relates to solid dosage forms of palbociclib comprising a water-soluble acid. The dosage forms described herein have desirable pharmacokinetic characteristics.

9 Claims, 4 Drawing Sheets

(51) Int. Cl.
A61K 9/28 (2006.01)
A61K 47/12 (2006.01)
A61K 31/4439 (2006.01)

(52) U.S. Cl.
CPC .......... *A61K 9/2013* (2013.01); *A61K 9/2018* (2013.01); *A61K 9/2027* (2013.01); *A61K 9/2054* (2013.01); *A61K 9/2086* (2013.01); *A61K 9/2095* (2013.01); *A61K 9/28* (2013.01); *A61K 31/4439* (2013.01); *A61K 47/12* (2013.01)

(56) References Cited

U.S. PATENT DOCUMENTS

| | | | |
|---|---|---|---|
| 7,345,171 | B2 | 3/2008 | Beylin et al. |
| 7,456,168 | B2 | 11/2008 | Barvian et al. |
| 7,781,583 | B2 | 8/2010 | Erdman et al. |
| 7,863,278 | B2 | 1/2011 | Beylin et al. |
| 2003/0149001 | A1* | 8/2003 | Barvian ............... A61K 31/519 514/80 |
| 2006/0183779 | A1 | 8/2006 | Brauns et al. |
| 2007/0141141 | A1 | 6/2007 | Bateman et al. |
| 2009/0214645 | A1 | 8/2009 | Kramer et al. |
| 2015/0140036 | A1 | 5/2015 | Mannick et al. |
| 2016/0002223 | A1 | 1/2016 | Chekal et al. |
| 2017/0281631 | A1 | 10/2017 | Wang et al. |
| 2018/0065964 | A1 | 3/2018 | Chekal et al. |

FOREIGN PATENT DOCUMENTS

| | | |
|---|---|---|
| JP | 2013189455 | 9/2013 |
| WO | 199808846 | 3/1998 |
| WO | 199823613 | 6/1998 |
| WO | 2003062236 | 7/2003 |
| WO | 2005005426 | 1/2005 |
| WO | 2008032157 | 3/2008 |
| WO | 2008032162 | 3/2008 |
| WO | 2013078264 | 5/2013 |
| WO | 2013092497 | 6/2013 |
| WO | 2014128588 | 8/2014 |
| WO | 2015022609 | 2/2015 |
| WO | 2016156070 | 10/2016 |
| WO | 2017166451 | 10/2017 |

OTHER PUBLICATIONS

A Pilot Study to Investigate The Effect of Concurrent Antacid Administration on The Bioavailability of Six Experimental Formulations of Palbociclib, Clinical trials.gov, Dec. 4, 2014.
Badawy & Hussain, Microenvironmental pH Modulation in Solid Dosage Forms, J. Pharm. Sci. (2007) 948-959.
Dvorackova et al., The Effect of Acid pH Modifiers on the Release Characteristics of Weakly Basic Drug from Hydrophlilic—Lipophilic Matrices, AAPS Pharm Sci Tech (2013) 14(4) 1341-1348.
International Preliminary Report on Patentability dated Dec. 5, 2017 for PCT/IB2016/053040, filed May 24, 2016 and Published on Dec. 8, 2016 as WO 2016/193860.
Sun et al., Impact of acid-reducing agents (ARAS) on the pharmacokinetics of palbociclib, a weak base with ph-dependent solubility, under differing food intake conditions, Eur. J. Cancer (2015) 51 Suppl.3, S59-S60, poster No. 315.
Sun et al., Impact of acid-reducing agents (ARAS) on the pharmacokinetics of palbociclib, a weak base with ph-dependent solubility, under differing food intake conditions, Clin. Pharmacol. Drug Dev. (2017) 6(6):614-626; Epub Apr. 21, 2017.
Colombia, pre-grant opposition by Laboratorio Franco Colombiano S.A.S. Lafrancol S.A.S., filed Jun. 22, 2018 (in Spanish).
Colombia, pre-grant opposition by Laboratorio Franco Colombiano S.A.S. Lafrancol S.A.S., filed Jun. 22, 2018 (English translation).
Dominican Republic, third party observations by Patent Opposition Project, filed Mar. 16, 2018 (in Spanish).
Ecuador, pre-grant opposition by Asociación de Laboratorios Farmacéuticos (ALAFAR), filed Jun. 21, 2018 (in Spanish).
Ecuador, pre-grant opposition by Asociación de Laboratorios Farmacéuticos (ALAFAR), filed Jun. 21, 2018 (English translation).
European Search Report dated Jan. 10, 2020 for European Patent Application No. EP19206647, filed Oct. 31, 2019.
Finn, R., et al., "PD 0332991, a selective cyclin D kinase 4/6 inhibitor, preferentially inhibits proliferation of luminal estrogen receptor-positive human breast cancer cell lines in vitro", Breast Cancer Research, 2009, pp. 1-13, 11(5): R77.
Fry, D., et al., "Specific inhibition of cyclin-dependent kinase 4/6 by PD 0332991 and associated antitumor activity in human tumor xenografts", Mol Cancer Ther, 2004, pp. 1427-1438, 3(11).
"Ibrance prescribing information"; retrieved from https://www.accessdata.fda.gov/drugsatfda_docs/label/2015/207103s000lbl.pdf Feb. 28, 2015.
"Ibrance prescribing information"; retrieved from https://www.accessdata.fda.gov/drugsatfda_docs/label/2019/212436lbl.pdf.
International Search Report dated Aug. 4, 2016 for PCT/IB2016/053040, filed May 24, 2016 and Published on Dec. 8, 2016 as WO 2016/193860.
Rugo, H., et al., "Endocrine Therapy for Hormone Receptor-Positive Metastatic Breast Cancer: American Society of Clinical Oncology Guideline", J Clin Oncol, 2016, pp. 3069-3103, 34(25).
Aulton ed., Pharmaceutics: The Science of Dosage Form Design, 2nd Edition (2002), pp. 127-129.
Aulton ed., Pharmaceutics: The Science of Dosage Form Design, 2nd Edition (2002), pp. 248-250.
Badawy & Hussain, Minireview: Microenvironmental pH Modulation in Solid Dosage Forms, J. Pharm. Sci. (2007), 96 (5):948-959.
Badawy, et al., Formulation of Solid Dosage Forms to Overcome Gastric pH Interaction of the Factor Xa Inhibitor, BMS-561389, Journal of Pharmaceutical Research (2006), 23(5):989-996.
Center for Drug Evaluation and Research Application No. 207103Orig1s000, Chemistry Review(s), Ibrance (palbociclib) capsules, 75, 100, and 125 mg, Jan. 20, 2015.
Chiwele, et al., The Shell Dissolution of Various Empty Hard Capsules, Chem. Pharm. Bull. (2000), 48(7):951-956.
CHMP, Assessment Report for Pradaxa (dabigatran etexilate), European Medicine Agency 2008.
Communication of a notice of opposition filed by Galenicum Health, S.L, from the European Patent Office dated Aug. 11, 2020 in related European Patent Application No. 16726192.4 filed May 24, 2016 and published as EP 3302565 on Apr. 11, 2018.
Communication of a notice of opposition filed by Generics [UK] Limited, from the European Patent Office dated Aug. 12, 2020 in related European Patent Application No. 16726192.4 filed May 24, 2016 and published as EP 3302565 on Apr. 11, 2018.
Communication of a notice of opposition filed by Hexal AG, from the European Patent Office dated Aug. 11, 2020 in related European Patent Application No. 16726192.4 filed May 24, 2016 and published as EP 3302565 on Apr. 11, 2018.
Communication of a notice of opposition filed by Hoffmann Eitle Patent-Und Rechtsanwalte PartmbB, from the European Patent Office dated Aug. 7, 2020 in related European Patent Application No. 16726192.4 filed May 24, 2016 and published as EP 3302565 on Apr. 11, 2018.
Communication of a notice of opposition filed by Synthon BV, from the European Patent Office dated Aug. 12, 2020 in related European Patent Application No. 16726192.4 filed May 24, 2016 and published as EP 3302565 on Apr. 11, 2018.
Communication of a notice of opposition filed by Teva Pharmaceutical Industries Ltd., from the European Patent Office dated Aug. 7, 2020 in related European Patent Application No. 16726192.4 filed May 24, 2016 and published as EP 3302565 on Apr. 11, 2018.
Consolidated list of cited opposition documents from the European Patent Office dated Aug. 6, 2020 in related European Patent Application No. 16726192.4 filed May 24, 2016 and published as EP 3302565 on Apr. 11, 2018.
Edelman, Breast Cancer Drug Found to be Ineffective in Treating Squamous Non-Small Cell Lung Cancer, cited Jun. 2, 2017, at

(56) References Cited

OTHER PUBLICATIONS https://www.foxchase.org/news/2017-06-02-ASCO-Edelman-palbociclib-ineffrective-squamous-non-small-cell-lung-cancer.
Felton ed., Remington: Essentials of Pharmaceutics (2013), p. 66-70.
Extract from the Register of European Patents for EP3302565, dated May 8, 2020. Available at https://register.epo.org/application?number=EP16726192.
Haddley, Palbociclib, Drugs of the Future (2013), 38(11):745-755.
Ibrance US label, Feb. 3, 2015. Available at: https://www.accessdata.fda.gov/drugsatfda_docs/label/2015/207103s000lbl.pdf.
Kibbe ed., Handbook of Pharmaceutical Excipients 3rd Edition (2000), pp. 102-106.
Kranz et al., Development of a single unit extended release formulation for ZK 811 752, a weakly basic drug, Eur. J. of Pharm. Sciences (2005), 26:47-53.
Niazi ed., Handbook of Bioequivalence Testing (2007), Ch. 1: BE Testing Rationale and Principle, p. 38-39, and Ch. 8: Drug Delivery Factors, pp. 217-218.
Niederhuber et al., eds., Abeloffs Clinical Oncology, 5th Edition (2014), p. 438.
Parikh ed., Handbook of Pharmaceutical Granulation Technology (1997), Ch. 13: Sizing of Granulation, pp. 389-418.
Qiu et al. eds., Developing Solid Oral Dosage Forms, 1st Edition (2009), Ch. 11 Oral absorption basics: pathways, physico-chemical and biological factors affecting absorption p. 284, and Ch. 16.4 Human Pharmacokinetic Evaluations p. 371.
Response dated Dec. 23, 2016 to communication from the European Patent Office dated Sep. 12, 2016 in related European Patent Application No. 14705884.6 filed Feb. 8, 2014 and published as EP 2958916 on Dec. 30, 2015.
Response dated Dec. 19, 2019 to communication from the European Patent Office dated Jun. 25, 2019 in related European Patent No. 2958916 B1 granted Sep. 12, 2018.
Ruiz-Garcia et al., Effect of Food on the Bioavailability of Palbocicib 125 Mg Capsules in Healthy Volunteers, Ann. Onc. (2014), 25(S4), abstract 463P.
Sateesha et al., Influence of Organic Acids on Diltiazem HCl Release Kinetics from Hydroxypropyl Methyl Cellulose Matrix Tablets, J. Young Pharm. (2010), 2(3)229-233.
Smith & Rawlins eds., Variability in Human Drug Response (1976), p. 26.
Swarbrick ed., Encyclopedia of Pharmaceutical Technology, Third Edition (2007), vol. 1, pp. 3653-3672.
Taniguchi et al., Microenvironmental pH-modification to improve dissolution behavior and oral absorption for drugs with pH-dependent solubility, Expert Opin. Drug Deliv. (2014), 11 (4):505-516.
European Patent Office, Decision of Tech. Bd. App. 3.3.02 of Jul. 7, 2011 (T 0007/07).
European Patent Office, Decision of Tech. Bd. App. 3.3.02 of Dec. 17, 2009 (T 0788/06).
Declaration of Dr. Fady Ibrahim dated Feb. 16, 2021 in related European Patent Application No. 16726192.4 filed May 24, 2016 and published as EP 3302565 on Apr. 11, 2018.
Huang et al., Fundamental aspects of solid dispersion technology for poorly soluble drugs, Acta Pharmaceutica Sinica B, (2014) 4(1): 18-25.
Kansara et al., Techniques used to Enhance Bioavailability of BCS Class II Drugs: A Review, Int. J. Drug Dev. & Res., (2015) 7(1): 82-93.
Kostewicz et al., Predicting the precipitation of poorly soluble weak bases upon entry in the small intestine, J. Pharmacy Pharmacol., (2004), 56:43-51.
Reply of the patent proprietor to the notice(s) of opposition dated Feb. 19, 2021 in related European Patent Application No. 16726192.4 filed May 24, 2016 and published as EP 3302565 on Apr. 11, 2018.
Tran et al., Dissolution-modulating mechanism of pH modifiers in solid dispersion containing weakly acidic or basic drugs with poor water solubility, Expert Opin. Drug Deliv, (2010) 7(5): 647-661.
U.S. Appl. No. 14/769,038, filed Feb. 8, 2014.
U.S. Appl. No. 15/808,577, filed Nov. 9, 2017.

* cited by examiner

SOLID DOSAGE FORMS OF PALBOCICLIB

Cross-Reference to Related Applications

This application is the U.S. National Phase under 35 U.S.C. 371 of Patent Cooperation Treaty Patent Application No. PCT/IB2016/053040, filed May 24, 2016, which claims the benefit of priority to U.S. Provisional Application No. 62/171,177, filed on Jun. 4, 2015 and U.S. Provisional Application No. 62/332,973, filed on May 6, 2016, the contents of which are incorporated by reference herein in their entirety.

BACKGROUND OF THE INVENTION

Field of the Invention

The present invention relates to solid dosage forms of 6-acetyl-8-cyclopentyl-5-methyl-2-(5-piperazin-1-yl-pyridin-2-ylamino)-8H-pyrido[2,3-d]pyrimidin-7-one (hereinafter palbociclib), having desirable pharmacokinetic characteristics which exhibit favorable storage stability and dissolution properties.

DESCRIPTION OF RELATED ART

Palbociclib is a potent and selective inhibitor of CDK4 and CDK6, having the structure:

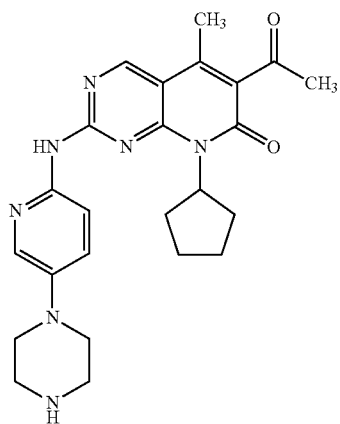 [SMILES: CC(=O)c1c(C)c2cnc(Nc3ccc(N4CCNCC4)cn3)nc2n(C2CCCC2)c1=O]

Palbociclib is described in *WHO Drug Information*, Vol. 27, No. 2, page 172 (2013). Palbociclib and pharmaceutically acceptable salts thereof are disclosed in International Publication No. WO 2003/062236 and U.S. Pat. Nos. 6,936,612, 7,208,489 and 7,456,168; International Publication No. WO 2005/005426 and U.S. Pat. Nos. 7,345,171 and 7,863,278; International Publication No. WO 2008/032157 and U.S. Pat. No. 7,781,583; and International Publication No. WO 2014/128588. The contents of each of the foregoing references are incorporated herein by reference in their entirety.

Palbociclib is approved in the United States for the treatment of hormone receptor (HR)-positive, human epidermal growth factor 2 (HER2)-negative advanced or metastatic breast cancer in combination with letrozole as initial endocrine therapy or in combination with fulvestrant following disease progression on endocrine therapy. The drug is sold by Pfizer under the trade name IBRANCE® in the form of an immediate release (IR) capsule dosage form comprising palbociclib as a free base for oral administration.

Palbociclib is a dibasic compound and has two basic groups with pKa's of approximately 7.3 (the secondary piperazine nitrogen) and 4.1 (the pyridine nitrogen). The solubility of palbociclib free base is pH dependent. Palbociclib is water soluble at low pH (2.1-4.5), while the solubility dramatically decreases as pH rises above 4.5. Palbociclib has poor water solubility (9 μg/mL) at pH 7.9. Concomitant administration of agents which increase gastric pH can alter the solubility and absorption of palbociclib free base formulations.

The absorption and bioavailability of a therapeutic agent can be affected by numerous factors when dosed orally, including whether the subject is in a fed or fasted state, and the use of certain medications, such as proton pump inhibitors (PPIs) or H2 receptor antagonists, as well as certain medical conditions. Compounds having pH-dependent solubility, particularly basic compounds, may exhibit undesirable pharmacokinetic properties, such as poor absorption and/or reduced bioavailability, which may result in significant inter-patient and intra-patient variability.

There remains a need to discover improved dosage forms of palbociclib having favorable dissolution and pharmacokinetic profiles, which also demonstrate good storage stability. We have surprisingly found that the solid dosage forms according to the present invention demonstrate excellent storage stability and provide substantially pH-independent delivery of palbociclib with no significant food effects or adverse interactions with PPIs.

BRIEF SUMMARY OF THE INVENTION

In a first aspect, the invention provides a solid dosage form comprising palbociclib, a water-soluble acid, and a pharmaceutically acceptable carrier.

In a second aspect, the invention provides a solid dosage form of any of the embodiments described herein, wherein the dosage form when added to a test medium comprising 500 mL of 10 mM pH 5.5 acetate buffer at 37° C. in a standard USP 2 rotating paddle apparatus with the paddles spinning at 50 rpm dissolves: (a) not less than 35% of the palbociclib in 15 minutes; (b) not less than 45% of the palbociclib in 30 minutes; (c) not less than 55% in 60 minutes; or (d) two or more of (a), (b) and (c).

In a third aspect, the invention provides a solid dosage form of any of the embodiments described herein, wherein the dosage form when added to a test medium comprising 500 mL of 50 mM pH 6.5 phosphate buffer and 0.1 M NaCl at 37° C. in a standard USP 2 rotating paddle apparatus with the paddles spinning at 50 rpm dissolves: (a) not less than 15% of the palbociclib in 15 minutes; (b) not less than 20% of the palbociclib in 30 minutes; (c) not less than 25% of the palbociclib in 60 minutes; or (d) two or more of (a),(b) and (c).

In some embodiments, the invention provides a solid dosage form of any of the embodiments described herein, wherein the dosage form when added to a test medium comprising 500 mL of 50 mM pH 6.5 phosphate buffer and 0.1 M NaCl at 37° C. in a standard USP 2 rotating paddle apparatus with the paddles spinning at 50 rpm dissolves: (a) not less than 20% of the palbociclib in 15 minutes; (b) not less than 30% of the palbociclib in 30 minutes; (c) not less than 25% of the palbociclib in 60 minutes; or (d) two or more of (a),(b) and (c).

In other embodiments, the invention provides a solid dosage form of any of the embodiments described herein, wherein the dosage form when added to a test medium comprising 500 mL of 50 mM pH 6.5 phosphate buffer and 0.1 M NaCl at 37° C. in a standard USP 2 rotating paddle apparatus with the paddles spinning at 50 rpm dissolves: (a) not less than 40% of the palbociclib in 15 minutes; (b) not less than 35% of the palbociclib in 30 minutes; (c) not less than 25% of the palbociclib in 60 minutes; or (d) two or more of (a),(b) and (c).

In a fourth aspect, the invention provides a solid dosage form of any of the embodiments described herein, wherein the dosage form: (a) has a mean fed/fasted ratio of the area under the plasma concentration versus time curve (AUC) from about 0.8 to about 1.25 after administration of a single oral dose to a subject; (b) has a mean fed/fasted ratio of the maximum plasma concentration ($C_{max}$) from about 0.8 to about 1.25 after administration of a single oral dose to a subject; or (c) both (a) and (b).

In a fifth aspect, the invention provides a solid dosage form of any of the embodiments described herein, wherein the dosage form: (a) provides a mean fasted AUC in the range of 80% to 125% of the mean fasted AUC for a control immediate release (IR) oral capsule containing an equivalent amount of palbociclib after administration of a single oral dose to a subject; or (b) provides a mean fasted $C_{max}$ in the range of 80% to 125% of the mean fasted $C_{max}$ for a control immediate release (IR) oral capsule containing an equivalent amount of palbociclib after administration of a single oral dose to a subject; or (c) both (a) and (b).

In a sixth aspect, the invention provides a solid dosage form of any of the embodiments described herein, wherein the dosage form: (a) provides a mean AUC in the presence of a proton pump inhibitor (PPI) in the range of 80% to 125% of the mean AUC in the absence of the PPI after administration of a single oral dose to a subject; (b) provides a mean $C_{max}$ in the presence of a proton pump inhibitor (PPI) in the range of 80% to 125% of the mean $C_{max}$ in the absence of the PPI after administration of a single oral dose to a subject; or (c) both (a) and (b). In some such embodiments, the PPI is rabeprazole.

In a seventh aspect, the invention provides a solid dosage form of any of the embodiments described herein, wherein the dosage form exhibits less than 0.3% acid adduct by weight after storage for 96 days at 30° C. and 75% relative humidity (RH).

In an eighth aspect, the invention provides a solid dosage form of any of the embodiments described herein, wherein the dosage form exhibits less than 1.0% acid adduct by weight after storage for 2 years at 30° C. and 75% RH.

In a ninth aspect, the invention provides a solid dosage form of any of the embodiments described herein, wherein the dosage form exhibits less than 0.05% acid adduct by weight after storage for 1 year at 25° C./60% RH. In some such embodiments, the dosage form is packaged with a desiccant canister in a bottle using a heat-induction seal.

In some embodiments of each of the aspects of the invention, the active pharmaceutical ingredient (API), palbociclib, comprises from about 10% to about 35% of the dosage form by weight. In specific embodiments, palbociclib comprises about 20% of the dosage form by weight.

In some embodiments of each of the aspects of the invention, the water-soluble acid comprises from about 5% to about 40% of the dosage form by weight. In particular embodiments, the water-soluble acid comprises from about 5% to about 25% of the dosage form by weight. In other embodiments, the water-soluble acid comprises from about 5% to about 15% of the dosage form by weight. In more particular embodiments, the water-soluble acid comprises about 10% of the dosage form by weight.

In some such embodiments, the water-soluble acid is selected from the group consisting of succinic acid, malic acid and tartaric acid. In specific embodiments, the water-soluble acid is succinic acid. In other embodiments, the water-soluble acid is malic acid. In further embodiments, the water-soluble acid is tartaric acid.

In a preferred embodiment of each of the aspects described herein, the solid dosage form comprises from about 10 wt % to about 35 wt % of palbociclib, from about 5 wt % to about 25 wt % of a water-soluble acid selected from the group consisting of succinic acid, malic acid and tartaric acid, and a pharmaceutically acceptable carrier. In particular embodiments, the water-soluble acid is succinic acid. In some such embodiments, the solid dosage form comprises about 20 wt % of palbociclib, about 10 wt % of succinic acid, and a pharmaceutically acceptable carrier.

In some embodiments of each of the aspects described herein, the pharmaceutically acceptable carrier comprises one or more of the following pharmaceutically acceptable excipients: diluents, disintegrants, binders, lubricants, glidants and surface-active agents. Such excipients may be incorporated into tablet forms either intragranularly or extragranularly, and tablets may comprise the same or different excipients as intragranular or extragranular components. For example, a tablet formulation may comprise an intragranular lubricant, an extragranular lubricant, or both an intragranular and an extragranular lubricant which may be the same or different.

In some embodiments of each of the aspects described herein, the pharmaceutically acceptable carrier comprises at least one diluent, wherein the diluent comprises about 50 wt % to about 75 wt % of the solid dosage form. In certain embodiments, the carrier comprises at least one diluent selected from the group consisting of microcrystalline cellulose, lactose monohydrate, mannitol, sorbitol, xylitol, magnesium carbonate, dibasic calcium phosphate and tribasic calcium phosphate. In specific embodiments, the diluent is microcrystalline cellulose. In some such embodiments, the diluent is microcrystalline cellulose.

In other embodiments of each of the aspects described herein, the pharmaceutically acceptable carrier comprises a lubricant, wherein the lubricant comprises from about 0.5 wt % to about 10 wt % of the solid dosage form. In certain embodiments, the carrier comprises at least one lubricant selected from the group consisting of magnesium stearate, calcium stearate, zinc stearate, and sodium stearyl fumarate. In specific embodiments, the lubricant is magnesium stearate, which may be included intragranularly, extragranularly, or both. In other embodiments, the lubricant is sodium stearyl fumarate. Other embodiments comprise both magnesium stearate and sodium stearyl fumarate as lubricants, which may be included intragranularly, extragranularly, or both.

In further embodiments of each of the aspects described herein, the pharmaceutically acceptable carrier comprises at least one disintegrant, wherein the disintegrant comprises from about 5 wt % to about 10 wt % of the solid dosage form. In certain embodiments, the carrier comprises at least one disintegrant selected from the group consisting of crospovidone, croscarmellose sodium and sodium starch glycolate. In specific embodiments, the disintegrant is crospovidone.

In frequent embodiments of each of the aspects described herein, the solid dosage form of the invention is in the form of a tablet. In some embodiments, the tablet is film coated. In some embodiments, the tablet is a monolayer tablet. In other embodiments, the tablet is a bilayer tablet. In particular embodiments, the tablets of the invention comprise palbociclib in the amount of 25 mg, 75 mg, 100 mg or 125 mg. In specific embodiments, the tablets of the invention comprise palbociclib in the amount of 125 mg.

The frequent embodiments of each of the aspects of the invention, the solid dosage form is in the form of a tablet. In some embodiments, the tablet is a monolayer tablet. In other embodiments, the tablet is a bilayer tablet.

In some embodiments of the aspects and embodiments described herein, the amount of palbociclib in the dosage form is 25 mg, 75 mg, 100 mg or 125 mg. In specific embodiments, the amount of palbociclib in the dosage form is 125 mg.

Each of the embodiments of the present invention described herein may be combined with one or more other embodiments of the present invention described herein that are not inconsistent with the embodiment(s) with which it is combined.

DETAILED DESCRIPTION OF THE INVENTION

Figure 1:
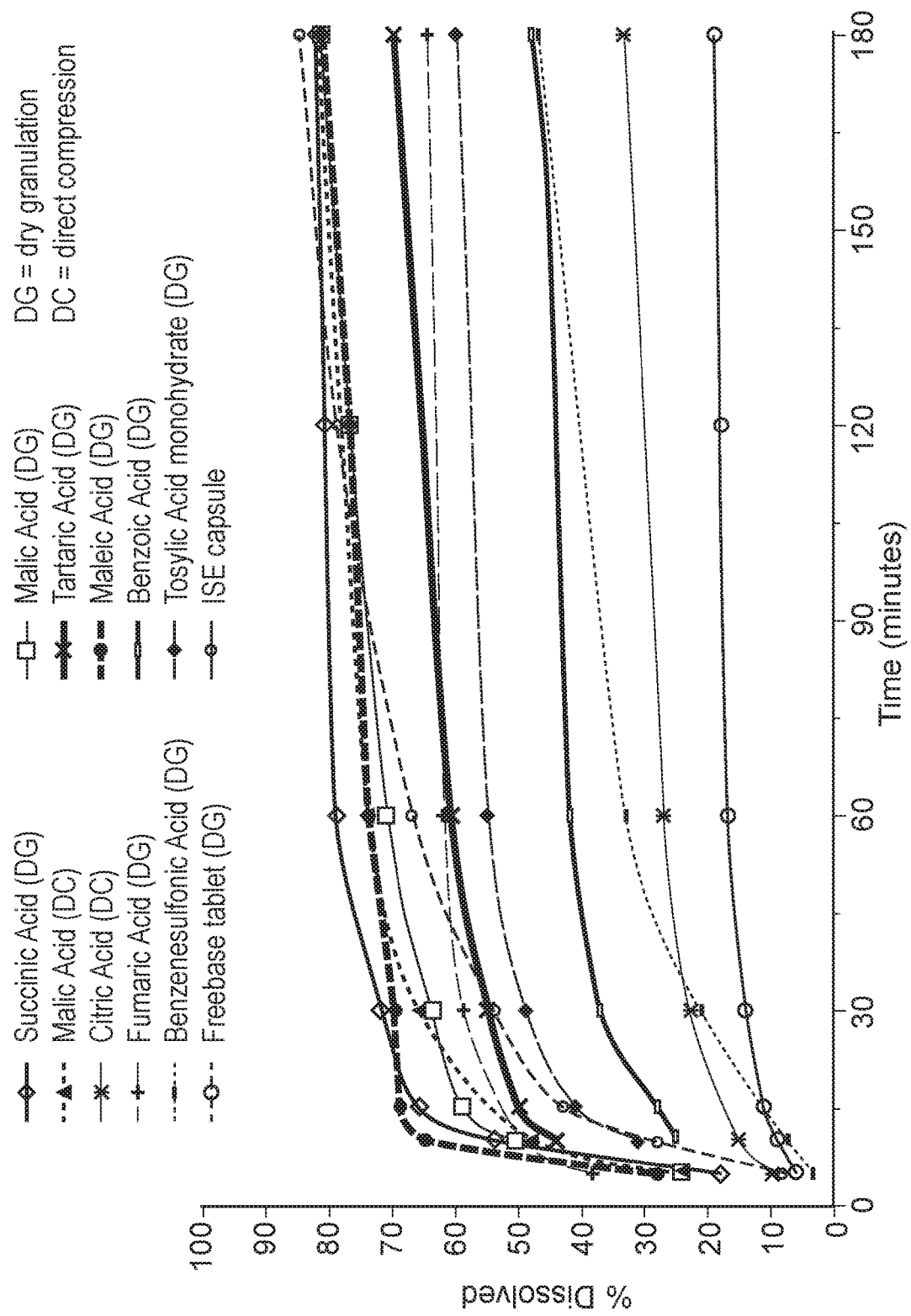
FIG. 1. In vitro dissolution data for prototype formulations comprising eight test water soluble acids (malic, maleic, succinic, fumaric, tartaric, tosylic, benzoic and benzenesulfonic acids) at 37° C. in a pH 5.5, 10 mM sodium acetate buffer solution in a USP 2 apparatus with paddles spinning at 50 rpm.

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "an" excipient includes one or more excipients.

The term "about" means having a value falling within an accepted standard of error of the mean when considered by one of ordinary skill in the art. Frequently, the term "about" refers to ±15%, preferably ±10%, and more preferably ±5% of the value or range to which it refers. For example, "about 10 wt %" means 10 wt % ±1.5 wt %, preferably 10 wt % ±1 wt %, and more preferably 10 wt % ±0.5 wt %.

Unless otherwise indicated herein, palbociclib refers the free base form of 6-acetyl-8-cyclopentyl-5-methyl-2-(5-piperazin-1-yl-pyridin-2-ylamino)-8H-pyrido[2,3-d]pyrimidin-7-one, which may be present in crystalline or amorphous form, or a mixture of amorphous and crystalline forms.

The absorption of orally administered drugs may be affected by changes in pH as the drug passes through the gastrointestinal (GI) tract. Absorption may occur at different locations along the GI tract, e.g., at the cheek lining, or in the stomach, duodenum, jejunum, ileum or colon. The pH differs at each site of absorption, with the pH of the stomach (pH 1-3.5) differing significantly from the pH of the small intestine (pH 4.5-8). Drugs having pH-dependent solubility may precipitate from solution as the drug passes through the GI tract, resulting in inter- or intra-patient variability in the extent and/or rate of absorption between doses or patients.

The pH of the GI tract may also vary based on whether a patient or subject is in a fed or fasted state. In general, the gastric residence time of a drug is longer in the presence of food than in the fasted state. If the bioavailability of a drug is significantly affected by the presence or absence of food in the GI tract, the drug is said to exhibit a "food effect". The rate of gastric emptying may also influence the concentration of drug in solution available for absorption at different sites along the GI tract.

Co-administration of certain medications, as well as medical conditions such as achlorhydria, may also affect the pH of the GI tract. The use of acid-reducing agents, such as proton pump inhibitors (PPIs) or H2 receptor antagonists, may result in a relatively high stomach pH, which can result in only partial dissolution of drugs having pH-dependent solubility in the stomach. Further dissolution of the undissolved drug may be inhibited by low solubility in the higher pH environment of the upper intestine. This can result in non-uniform dissolution of drugs having pH-dependent solubility, increasing the risk of drug-drug interactions, and potentially leading to decreased absorption and reduced therapeutic benefit.

A study in healthy volunteers showed that exposure with palbociclib treatment (125 mg administered once daily as a free base capsule) was marginally increased in fed (AUCinf, 23%-27%; Cmax, 21%-24%) versus fasted (AUCinf, 39%; Cmax, 73%) subjects, and PK variability was greatly reduced in the fed state. Ruiz-Garcia et al., Annals of Oncology (2014) 25 (suppl_4): iv146-iv164. 10.1093/annonc/mdu331. Because of the reduced inter-patient variability observed in the fed state, it is recommended on the U.S. package insert that commercial free base capsules of palbociclib be taken with food.

When formulating a compound into a tablet or other solid dosage form, it is desirable to develop a formulation which is storage stable at temperatures and relative humidity levels above those typically encountered. Other desirable properties in a formulation may also be sought, such as fast dissolution so that the tablet quickly dissolves and the drug is available for absorption. Accordingly, good storage stability and fast dissolution were, inter alia, features that were sought as desirable characteristics for the instant invention.

Drug dissolution represents a critical factor affecting the rate of systemic absorption. A variety of in vitro methods have been developed for assessing the dissolution properties of pharmaceutical formulations, and dissolution testing is sometimes used as a surrogate for the direct evaluation of drug bioavailability. See, e.g., Emmanuel et al., *Pharmaceutics* (2010), 2:351-363, and references cited therein. Dissolution testing measures the percentage of the API that has been released from the drug product (i.e., tablet or capsule) and dissolved in the dissolution medium under controlled testing conditions over a defined period of time. To maintain sink conditions, the saturation solubility of the drug in the dissolution media should be at least three times the drug concentration. For low solubility compounds, dissolution may sometimes be determined under non-sink conditions. Dissolution is affected by the properties of the API (e.g., particle size, crystal form, bulk density), the composition of the drug product (e.g., drug loading, excipients), the manufacturing process (e.g., compression forces) and the stability under storage conditions (e.g., temperature, humidity).

Methods for assessing the chemical storage stability of solid dosage forms under accelerated aging conditions have been described in the literature. See, e.g., S. T. Colgan, T. J. Watson, R. D. Whipple, R. Nosal, J. V. Beaman, D. De Antonis, "The Application of Science and Risk Based Concepts to Drug Substance Stability Strategies" J. Pharm. Innov. 7:205-2013 (2012); Waterman K C, Carella A J, Gumkowski M J, et al. Improved protocol and data analysis for accelerated shelf-life estimation of solid dosage forms. Pharm Res 2007; 24(4):780-90; and S. T. Colgan, R. J. Timpano, D. Diaz, M. Roberts, R. Weaver, K. Ryan, K. Fields, G. Scrivens, "Opportunities for Lean Stability Strategies" J. Pharm. Innov. 9:259-271 (2014).

For the solid dosage forms of the present invention, the formation of an acid adduct of the piperazinyl moiety of palbociclib and the water-soluble acid is a key degradant that is monitored to assess storage stability.

As further described herein, the present invention provides solid dosage forms comprising palbociclib, a water-soluble acid, and a pharmaceutically acceptable carrier, and methods for their production and use.

Solid dosage forms include, but are not limited to, immediate release tablets and capsules, controlled-release (CR) tablets and capsules, fast-dissolve dosage forms, chewable dosage forms, sachets, etc. Preferably, the dosage form of the present invention is in the form of a tablet, including monolayer or bilayer tablets.

A "solid dosage form" of the present invention is a pharmaceutically-acceptable solid dosage form that is safe for oral administration to humans, where all excipients in the dosage form are pharmaceutically acceptable for use in oral formulations, in other words safe for human ingestion. In frequent embodiments, the solid dosage form is a tablet.

As used herein, the term "unit dose" or "unit dosage" refers to a physically discrete unit that contains a predetermined quantity of active ingredient calculated to produce a desired therapeutic effect. The unit dose or unit dosage may be in the form of a tablet, capsule, sachet, etc. referred to herein as a "unit dosage form."

The term "fasted" as used herein is defined as follows: the dosing state which is defined following an overnight fast (wherein 0 caloric intake has occurred) of at least 10 hours (i.e., ≥10 hours). Subjects may administer the dosage form with 240 mL of water. No food should be allowed for at least 4 hours post-dose. Water may be allowed as desired except for one hour before and after drug administration.

The term "fed" as used herein is defined as follows: the dosing state which is defined following an overnight fast (wherein 0 caloric intake has occurred) of at least 10 hours, subjects then begin the recommended meal. Subjects should eat this meal in 30 minutes or less; however the drug product should be administered 30 minutes after the start of the meal. The drug product may be administered with 240 mL of water. No food should be allowed for at least 4 hours post-dose. Water may be allowed as desired except for one hour before and after drug administration.

To assess the fed/fasted ratio, a single oral dose of palbociclib may be administered: 30 minutes after a high-fat, high-calorie meal (~800-1000 calories with 150, 250, and 500-600 calories from protein, carbohydrate, and fat, respectively); 30 minutes after a low-fat, low-calorie meal (~400-500 calories with 120, 250, and 28-35 calories from protein, carbohydrate, and fat, respectively); or between meals (1 hour after/2 hours before) for a moderate fat and calorie content meal (~500-700 calories consisting of 15% protein, 50% carbohydrate, and 35% fat).

A high fat and high calorie meal may be used as the test meal under the fed condition. An example high fat test meal would be two eggs fried in butter, two strips of bacon, two slices of toast with butter, four ounces of hash brown potatoes and eight ounces of whole milk.

The calculation of the mean area under the serum concentration versus time curve (AUC) is a well-known procedure in the pharmaceutical arts and is described, for example, in Welling, "Pharmacokinetics Processes and Mathematics," ACS Monograph 185 (1986). AUC as used herein includes area under the concentration-time curve from time zero extrapolated to infinite time following a single dose or the area under the concentration-time curve from time zero to time of the end of dosing interval following steady state/multiple doses.

In addition, the calculations for $C_{max}$, $C_{min,ss}$, $T_{max}$, and elimination half-life (t½), are also known to this of ordinary skill in the art and is described, for example, in Shargel, Wu-Pong, and Yu, Applied Biopharmaceutics and Pharmacokinetics (2005).

To determine the mean fed/fasted ratio, the individual ratio of the mean area under the plasma concentration versus time curve of palbociclib (e.g. $AUC_{0-inf}$) in the fed state to the mean area under the plasma concentration versus time curve of palbociclib (e.g. $AUC_{0-inf}$) in the fasted state is first calculated, and then the corresponding individual ratios are averaged together. In this way, it is the average of each corresponding individual's ratio which is determined.

Proton-pump inhibitors (PPIs) are a well-known class of drugs that reduce the production of gastric acid, thereby modifying gastric pH. Representative PPIs include, for example, rabeprazole, omeprazole (including S- and B-forms, Na and Mg salts), lansoprazole, pantoprazole, esomeprazole, and the like.

As used herein, the term "control immediate release (IR) oral capsule" refers to the commercial IR capsule formulation of palbociclib as described in Example 11. This formulation, along with an isethionate salt formulation (ISE) and a free base tablet dosage form that lacks the water-soluble acid but is otherwise substantially the same as the formulation in Example 1 may be referenced herein as controls.

"Dissolution Test 1" refers to the following test of dosage forms of palbociclib. The dissolution test is conducted in a standard USP 2 rotating paddle apparatus as disclosed in United States Pharmacopoeia (USP) Dissolution Test Chapter 711, Apparatus 2. Paddles are rotated at 50 rpm and the dosage form is added to 500 mL of 10 mM pH 5.5 acetate buffer at 37° C. At appropriate times following test initiation (e.g., insertion of the dosage form into the apparatus), filtered aliquots (typically 1.5 mL) from the test medium are analyzed for palbociclib by high performance liquid chromatography (HPLC). Dissolution results are reported as the percent of the total dose of palbociclib tested dissolved versus time.

"Dissolution Test 2" refers to the following test of dosage forms of palbociclib. The dissolution test is conducted in a standard USP 2 rotating paddle apparatus as disclosed in United States Pharmacopoeia (USP) Dissolution Test Chapter 711, Apparatus 2. Paddles are rotated at 50 rpm and the dosage form is added to 500 mL of 50 mM pH 6.5 phosphate buffer and 0.1 M NaCl at 37° C. At appropriate times following test initiation (e.g., insertion of the dosage form into the apparatus), filtered aliquots (typically 1.5 mL) from the test medium are analyzed for palbociclib by high performance liquid chromatography (HPLC). Dissolution results are reported as the percent of the total dose of palbociclib tested dissolved versus time.

The term "dry granulation" means the process of blending bulk active product with at least one excipient. The blend is then compressed, or compacted, to form a compressed material or "compact". This material may be broken apart to form granules by crushing, grinding or cutting into dry granulated particles. Optionally, the particles may be further processed. Crushing, grinding, or cutting processes involve an operation that reduces the size of the compressed material such as accomplished by milling or by other operations known to those skilled in the art.

The term "water-soluble" used herein in relation to the acid present in the composition refers to an acid that has a solubility of at least 0.2% by weight in water at 25° C. The water-soluble acid may be an organic or inorganic acid, and preferably is an organic acid having at least one pKa value which is at least one (preferably at least two) pK unit lower than the highest pKa of the basic groups present in the drug. In the case of the palbociclib, which has pKa values of approximately 4.1 and 7.3, the acid preferably has a pKa of less than 6.3, and more preferably a pKa of less than 5.3. Water-soluble organic acids include, for example, $C_2$-$C_8$ or $C_2$-$C_6$ aliphatic mono or poly-carboxylic acids, and preferably $C_4$-$C_6$ aliphatic mono or poly-carboxylic acids. Particularly preferred are $C_4$-$C_6$ dicarboxylic acids, which may be saturated or unsaturated.

Solid dosage forms of the invention may comprise a single water-soluble acid, or may include a combination of two or more such acids. In selected embodiments of the invention, the water-soluble acid is selected from the group consisting of succinic acid, malic acid and tartaric acid. In certain preferred embodiments of the invention, the water-soluble acid is succinic acid.

The water-soluble acid may be combined with the drug prior to granulation or it may be incorporated into the dosage form along with extragranular excipients. In a bilayer tablet, the water-soluble acid may be present in the active layer containing palbociclib, incorporated into a separate acid layer, or water-soluble acids (which may be the same or different) may be incorporated into both the active and acid layers.

Without wishing to be bound by theory, it is thought that the presence of an acid in the solid dosage form in close contact with the drug increases solubilization by way of an interaction between palbociclib and the acid. The solid dosage forms of the invention thereby provide an increased local concentration of the drug in solution following oral administration to a subject as compared to administration of palbociclib formulations lacking the water-soluble acid.

In some embodiments, the solid dosage form of any of the embodiments described herein, under the conditions of Dissolution Test 1 (pH 5.5 acetate buffer, 37° C.), dissolves: (a) not less than 35% of the palbociclib in 15 minutes; (b) not less than 45% of the palbociclib in 30 minutes; (c) not less than 55% in 60 minutes; or (d) two or more of (a), (b) and (c).

In further embodiments, the solid dosage form of the invention under the conditions of Dissolution Test 1 dissolves: (a) not less than 25%, 30%, 35%, 40%, 45%, or 50%, or more than 50% of the palbociclib is dissolved in 15 minutes; (b) not less than 35%, 40%, 45%, 50%, 55%, or 60%, or more than 60% of the palbociclib is dissolved in 30 minutes; and/or (c) not less than 45%, 50%, 55%, 60%, 65%, or 70% or more than 70% of the palbociclib is dissolved in 60 minutes.

In some embodiments, the solid dosage form of any of the embodiments described herein, under the non-sink conditions of Dissolution Test 2 (pH 6.5 phosphate buffer and 0.1 M NaCl, 37° C.) dissolves: (a) not less than 40% of the palbociclib in 15 minutes; (b) not less than 35% of the palbociclib in 30 minutes; (c) not less than 25% of the palbociclib in 60 minutes; or (d) two or more of (a),(b) and (c).

In other embodiments, the solid dosage form of any of the embodiments described herein, under the non-sink conditions of Dissolution Test 2 (pH 6.5 phosphate buffer and 0.1 M NaCl, 37° C.) dissolves: (a) not less than 15% of the palbociclib in 15 minutes; (b) not less than 20% of the palbociclib in 30 minutes; (c) not less than 25% of the palbociclib in 60 minutes; or (d) two or more of (a),(b) and (c).

In other embodiments under Dissolution Test 2: (a) not less than 10%, 15%, 20%, 25%, 30%, 35%, 40%, 45%, or 50%, or more than 50% of the palbociclib is dissolved in 15 minutes; (b) not less than 15%, 20%, 25%, 30%, 35%, 40%, 45%, or 50%, or more than 50% of the palbociclib is dissolved in 30 minutes; and/or (c) not less than 15%, 20%, 25%, 30%, 35%, or 40%, or more than 40% of the palbociclib is dissolved in 60 minutes.

In further embodiments under Dissolution Test 2: (a) not less than 30%, 35%, 40%, 45%, or 50%, or more than 50% of the palbociclib is dissolved in 15 minutes; (b) not less than 25%, 30%, 35%, 40%, 45%, or 50%, or more than 50% of the palbociclib is dissolved in 30 minutes; and/or (c) not less than 15%, 20%, 25%, 30%, 35%, or 40%, or more than 40% of the palbociclib is dissolved in 60 minutes.

In some embodiments, the invention provides a solid dosage form comprising palbociclib, a water-soluble acid, and a pharmaceutically acceptable carrier, wherein the dosage form provides: (a) a mean fed/fasted ratio of the area under the plasma concentration versus time curve (AUC) from about 0.8 to about 1.25 after administration of a single oral dose to a subject; (b) a mean fed/fasted ratio of the maximum plasma concentration ($C_{max}$) from about 0.8 to about 1.25 after administration of a single oral dose to a subject; or (c) both (a) and (b).

In some embodiments, the invention provides a solid dosage form comprising palbociclib, a water-soluble acid, and a pharmaceutically acceptable carrier, wherein the dosage form provides: (a) a mean fasted AUC in the range of 80% to 125% of the mean fasted AUC for a control immediate release (IR) oral capsule containing an equivalent amount of palbociclib after administration of a single oral dose to a subject; (b) a mean fasted $C_{max}$ in the range of 80% to 125% of the mean fasted $C_{max}$ for a control immediate release (IR) oral capsule containing an equivalent amount of palbociclib after administration of a single oral dose to a subject; or (c) both (a) and (b).

In further embodiments, the invention provides a solid dosage form comprising palbociclib, a water-soluble acid, and a pharmaceutically acceptable carrier, wherein the dosage form provides: (a) a mean AUC in the presence of a proton pump inhibitor (PPI), preferably rabeprazole, in the range of 80% to 125% of the mean AUC in the absence of the PPI after administration of a single oral dose to a subject; (b) a mean $C_{max}$ in the presence of a proton pump inhibitor (PPI), preferably rabeprazole, in the range of 80% to 125% of the mean $C_{max}$ in the absence of the PPI after administration of a single oral dose to a subject; or (c) both (a) and (b).

In other embodiments, the invention provides a solid dosage form comprising palbociclib, a water-soluble acid, and a pharmaceutically acceptable carrier, wherein the dosage form exhibits less than 0.4%, 0.35%, 0.3%, 0.25%, 0.2%, 0.15% or 0.1% acid adduct by weight after storage for 96 days at 30° C. and 75% relative humidity (RH).

In still other embodiments, the invention provides a solid dosage form comprising palbociclib, a water-soluble acid, and a pharmaceutically acceptable carrier, wherein the dosage form exhibits less than 1.5%, 1.4%, 1.3%, 1.2%, 1.1%, 1.0%, 0.9%, 0.8%, 0.7%, 0.6%, 0.5%, 0.4% or 0.3% acid adduct by weight after storage for 2 years at 30° C. and 75% RH.

In some embodiments of each of the aspects and embodiments of the invention, the water-soluble acid is selected from the group consisting of succinic acid, malic acid and tartaric acid. In specific embodiments of each of the aspects and embodiments herein, the water-soluble acid is succinic acid. In other embodiments, the water-soluble acid is malic acid. In further embodiments, the water-soluble acid is tartaric acid.

In some embodiments of each of the aspects of the invention, the water-soluble acid comprises from about 5% to about 40% of the dosage form by weight. In particular embodiments, the water-soluble acid comprises from about 5% to about 25% of the dosage form by weight. In some embodiments, the water-soluble acid comprises about 5%, 10%, 15%, 20%, 25%, 30%, 35% or 40% of the dosage form by weight.

In some embodiments of each of the aspects of the invention, palbociclib comprises from about 10% to about 35% of the dosage form by weight. In specific embodiments, palbociclib comprises about 20% of the dosage form by weight. In some embodiments, the palbociclib comprises about 5%, 10%, 15%, 20%, 25%, 30%, 35%, 40%, 45% or 50% of the dosage form by weight.

In frequent embodiments of each of the aspects and embodiments herein, the solid dosage form is a tablet, preferably a tablet formed by dry-granulation. In some such embodiments, the tablet is a bilayer tablet. In particular embodiments, the bilayer tablet comprises: (a) an active layer comprising palbociclib and a pharmaceutically acceptable carrier; and (b) an acid layer comprising a water-soluble acid and a pharmaceutically acceptable carrier. In some embodiments, the bilayer tablet comprises: (a) an active layer comprising palbociclib, a water-soluble acid, and a pharmaceutically acceptable carrier; and (b) an acid layer comprising a water-soluble acid and a pharmaceutically acceptable carrier, wherein the water-soluble acid in the active layer may be the same or different than the water-soluble acid in the acid layer. In a specific embodiment, the water-soluble acid in the active layer is succinic acid and the water-soluble acid in the acid layer is tartaric acid.

In another aspect, the invention provides a method of treating cancer comprising administering to a subject in need thereof a therapeutically effective amount of the solid dosage form of any of the aspects and embodiments described herein. In particular embodiments, the cancer is breast cancer. In some such embodiments, the breast cancer is hormone-receptor positive (HR+) breast cancer. In some such embodiments, the breast cancer is estrogen-receptor positive (ER+) breast cancer. In some such embodiments, the breast cancer is human epidermal growth factor receptor 2 negative (HER−) breast cancer. In other such embodiments, the breast cancer is human epidermal growth factor receptor 2 positive (HER+) breast cancer. In further embodiments, the breast cancer is advanced or metastatic breast cancer, which may be characterized as HR+, HER2− or ER+, HER2−.

Palbociclib may be administered alone or in combination with other drugs, in particular aromatase inhibitors, e.g., letrozole, fulvestrant or exemestane, and will generally be administered as a formulation in association with one or more pharmaceutically acceptable excipients. The term "excipient" describes any ingredient other than palbociclib or a salt thereof.

Palbociclib may be administered orally. Oral administration may involve swallowing, so that the compound enters the gastrointestinal tract, or buccal or sublingual administration may be employed by which the compound enters the blood stream directly from the mouth.

A therapeutically effective amount of dosage form of the invention may be administered to a subject in need of such treatment. The term "therapeutically effective amount" as used herein refers to that amount of a compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, and/or (4) relieving to some extent (or, preferably, eliminating) one or more signs or symptoms associated with the cancer.

As used herein, "subject" refers to a human or animal subject. In certain preferred embodiments, the subject is a human. In some embodiments, the subject is a patient afflicted with a disease state. In other embodiments, the subject may be a healthy volunteer.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as defined immediately above. The term "treating" also includes adjuvant and neo-adjuvant treatment of a subject. Palbociclib may be administered alone, or in combination with an aromatase inhibitor, such as letrozole, fulvestrant or exemestane.

As used herein "cancer" refers to any malignant and/or invasive growth or tumor caused by abnormal cell growth. As used herein "cancer" refers to solid tumors named for the type of cells that form them (e.g., breast cancer), and cancers of blood, bone marrow, or the lymphatic system. Examples of solid tumors include but not limited to sarcomas and carcinomas. Examples of cancers of the blood include but not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one.

More specifically, examples of cancer in connection with the present invention include, inter alia, breast cancer, preferably in combination with an aromatase inhibitor. For example, the cancer may be hormone receptor positive (HR+) breast cancer, and in particular estrogen receptor positive (ER+) breast cancer. In some embodiments, said ER+breast cancer is human epidermal growth factor 2 (HER2)-negative. In further embodiments, the cancer is ER+, HER2− advanced metastatic breast cancer, wherein the drug is administered in combination with an aromatase inhibitor for treatment of metastatic disease.

Formulations suitable for oral administration include solid formulations such as tablets, capsules, powders, lozenges (including liquid-filled), sachets and the like. In a preferred aspect of the invention, the solid dosage form provided herein is a tablet. In some such embodiments, the tablet is film coated. In other such embodiments, the tablet is a bilayer tablet.

For tablet dosage forms, depending on dose, palbociclib may make up from 1 wt % to 80 wt % of the dosage form, typically from 5 wt % to 60 wt %, more typically from about 10 wt % to about 35 wt %, or even more typically from about 15 wt % to about 25 wt % of the dosage form. In specific embodiments, palbociclib comprises about 20 wt % of the dosage form by weight.

In the solid dosage forms of the invention, the carrier may comprise a variety of pharmaceutically acceptable excipients, including, for example, diluents, disintegrants, binders, lubricants, glidants and surface-active agents. Formulations may also include excipients such as preservatives, antioxidants, flavors and colorants, as well as other excipients known in the art.

Solid dosage forms, such as tablets, typically contain diluents, e.g., lactose (monohydrate, spray-dried monohydrate, anhydrous and the like), mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers, polyethylene oxide, hydroxypropyl methyl cellulose and mixtures thereof. Different types of microcrystalline cellulose may be suitable for use in the formulations described herein. Examples of microcrystalline cellulose include Avicel® types: PH101, PH102, PH103, PH105, PH 112, PH113, PH200, PH301, and other types of microcrystalline cellulose, such as silicified microcrystalline cellulose (SMCC). In some embodiments, the diluent is selected from the group consisting of microcrystalline cellulose, lactose monohydrate, mannitol, sorbitol, xylitol, magnesium carbonate, dibasic calcium phosphate, tribasic calcium phosphate, or mixtures thereof. In certain embodiments, the diluent comprises microcrystalline cellulose. In some embodiments, the diluent comprises one or more types of microcrystalline cellulose, for example Avicel® PH105, Avicel® PH200 or mixtures thereof. In some such embodiments, the diluent excludes lactose monohydrate. In other such embodiments, the diluent comprises microcrystalline cellulose and further comprises lactose monohydrate. Diluents frequently comprise from about 25 wt % to about 75 wt % of the solid dosage form, and preferably from about 50 wt % to about 75 wt % of the dosage form.

Solid dosage forms frequently contain disintegrants. Examples of disintegrants include sodium starch glycolate, sodium carboxymethyl cellulose, calcium carboxymethyl cellulose, croscarmellose sodium, crospovidone, polyvinylpyrrolidone, methylcellulose, microcrystalline cellulose, lower alkyl-substituted hydroxypropyl cellulose, starch, pregelatinized starch, and sodium alginate. In some embodiments, the disintegrant is crospovidone. Any grade of crospovidone can be used; for example CL, CL-SF and XL grades of crospovidone are suitable for use in the formulations described herein. Specific examples include Kollidon, Kollidon CL®, Kollidon CL-M®, Polyplasdone XL®, Polyplasdone XL-10®, and Polyplasdone INF-10®. In some embodiments, the carrier comprises at least one disintegrant selected from the group consisting of crospovidone, croscarmellose sodium and sodium starch glycolate. In specific embodiments, the disintegrant is crospovidone. Disintegrants frequently comprise from about 1 wt % to about 25 wt %, preferably from about 5 wt % to about 20 wt %, more preferably from about 5 wt % to about 10 wt % of the dosage form.

Binders may be used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose, and hydroxypropyl methylcellulose. In some embodiments, the binder is selected from the group consisting of microcrystalline cellulose, hydroxypropyl cellulose and hydroxypropyl methylcellulose. In specific embodiments, the binder is microcrystalline cellulose, e.g. Avicel® PH105. When present, binders may comprise from about 0 wt % to about 15 wt %, or from about 0.2 wt % to about 10 wt % of the dosage form. In some embodiments, the binder comprises about 5 wt % to about 10 wt % of the dosage form. In particular embodiments, the binder comprises about 10 wt % of the dosage form.

Solid dosage forms frequently contain one or more lubricants. Examples of lubricants include magnesium stearate, calcium stearate, zinc stearate, sodium stearyl fumarate, mixtures of magnesium stearate with sodium lauryl sulfate, or mixtures of two or more of these. In some embodiments, the lubricant is magnesium stearate and/or sodium stearyl fumarate. In some embodiments, the lubricant is magnesium stearate. In some such embodiments, the solid dosage form is a tablet comprising intragranular and extragranular magnesium stearate. In other embodiments, the solid dosage form is a tablet comprising intragranular magnesium stearate and extragranular sodium stearyl fumarate. When present, lubricants frequently comprise from about 0.25 wt % to about 10 wt %, preferably from about 0.5 wt % to about 6 wt % of the dosage form.

Tablets may also compromise glidants, for example silicon dioxide, colloidal silicon dioxide, magnesium silicate, magnesium trisilicate, talc, and other forms of silicon dioxide, such as aggregated silicates and hydrated silica. In some embodiments, the glidant is silicon dioxide. When present, glidants may comprise from about 0 wt % to about 10 wt %, preferably from about 0.2 wt % to about 5 wt %, or from about 0.5 wt % to about 2 wt % of the tablet.

Tablets may optionally include surface-active agents, such as sodium lauryl sulfate and polysorbate 80. When present, surface-active agents may comprise from 0 wt % to 10 wt %, or preferably 0.2 wt % to 5 wt % of the tablet.

In general, the solid dosage forms of the invention are prepared according to methods usual in pharmaceutical chemistry. Selected excipients may be incorporated along with the API into either or both of the extragranular or intragranular compartments.

Exemplary tablet formulations contain from about 10 wt % to about 35 wt % palbociclib, typically from about 15 wt % to about 25 wt % palbociclib; from about 5 wt % to about 15 wt % water-soluble acid; from about 25 wt % to about 75 wt % diluent; from about 5 wt % to about 10 wt % disintegrant; from about 0.5 wt % to about 6 wt % lubricant; and optionally from about 0 wt % to about 5 wt % glidant, and from about 0 wt % to about 15 wt % binder.

Further exemplary tablet formulations contain about 20 wt % palbociclib; about 10 wt % water-soluble acid, preferably succinic acid; from about 50 wt % to about 75 wt % diluent, preferably microcrystalline cellulose; from about 5 wt % to about 10 wt % disintegrant, preferably crospovidone; from about 0.5 wt % to about 6 wt % lubricant, preferably magnesium stearate or sodium stearyl fumarate, or both; optionally from about 0 wt % to about 5 wt % glidant; and optionally from about 0 wt % to about 15 wt % binder. When present, the glidant is preferably silicon dioxide and the binder is preferably microcrystalline cellulose of an appropriate type (e.g., Avicel® PH105) as a dry binder.

Solid formulations for oral administration may be formulated to be immediate and/or modified release. Modified release formulations include delayed-, sustained-, pulsed-, controlled-, targeted-, and programmed-release. For a general description of modified release formulations, see U.S. Pat. No. 6,106,864.

Pharmaceuticals in the form of solid shaped tablets are typically manufactured by compressing the materials that make up the final product into the desired tablet form. Such materials may include active pharmaceutical ingredients as well as pharmaceutically non-active excipients that impart necessary or useful properties to the product during and after the manufacturing process. Tablet hardness, or tensile strength can be used as a measure of the cohesiveness of the ingredients of a tablet. If a tablet does not possess sufficient cohesive properties the tablet may fall apart on handling. The final formulation may comprise one or more layers and may be coated or uncoated.

As is known in the art, granulation is a process used to improve the handling and manufacturing properties of a formulation, for example by increasing particle size to improve flow. Granulation does not substantially change the physical form of the drug such as its crystalline or amorphous character. Various processes are used by those of skill in the art for preparing tablet dosage forms. Examples of such processes include dry-granulation, wet-granulation, fluid-bed granulation and direct compression. The type of method used may depend upon factors such as physical characteristics of the active pharmaceutical ingredients in the formulation, the types of excipients used and the desired physical characteristics of the final product. Each of these processes include steps involving mixing of the ingredients of the dosage form. In certain embodiments of the present invention, dry-granulation is preferred.

Some amount of mixing of the ingredients of a dosage form is usually necessary in order to have a homogeneous and consistent final product. However, in the preparation of pharmaceutical tablets by wet and dry granulation it has been found that the extent and intensity of the mixing of the ingredients prior to compression is related to a loss of compressibility and cohesiveness of the formulation, resulting in reduced tablet hardness.

A similar result may be observed when roller compaction is used, for example, in dry granulation methods. Roller compaction may be employed as a method to form the granules that are subsequently compressed into tablets. Roller compaction may reduce the subsequent compressibility and cohesiveness of the dosage form.

Dry granulation is a process in which granulates are formed by a compaction step that is followed by sizing the compacts into particles that can be processed easily. It is often used to improve flow properties and/or densify the formulation which can facilitate further manufacturing processes such as tableting, encapsulation and powder filling. The compacts are made directly from powder blends that usually contain an active ingredient and other excipients including a lubricant.

The use of dry granulation techniques may be preferred to wet granulation methods because of shorter processing times and cost advantages. However, dry granulation is generally limited to those situations in which the drug or active ingredient has physical characteristics suitable for forming pharmaceutically acceptable granulations and dosage forms such as tablets.

The addition of at least one excipient to the formulation is generally required and will contribute to increasing the tablet size of the final product. As tablet size must be within certain parameters to function as a suitable dosage form, there is a limit beyond which increasing tablet size to accommodate increasing amounts of excipients to enhance compactability is not practical. As a result, manufacturers are often limited to using the dry granulation method for formulations containing a low dose of the active ingredient per compressed tablet such that the formulation may accommodate sufficient levels of excipient to make dry granulation practical.

In the development of pharmaceutical dosage forms, it is important to balance several different objectives. It is important to prepare a pharmaceutical dosage form as economically as possible. It would be desirable to have a simple production method comprising a few processing steps. The dosage form should also optimally make available the active compound contained therein to the patient. Further, the dosage form should be easy to swallow. Smaller dosage forms are better accepted by patients and increase patient compliance.

The final pharmaceutical composition is processed into a unit dosage form (e.g., tablet or capsule) and then packaged for distribution. The processing step will vary depending upon the particular unit dosage form. For example, a tablet is generally compressed under pressure into a desired shape and a capsule employs a simple fill operation. Those skilled in the art are well aware of the procedures used for manufacturing the various unit dosage forms.

Tablets are typically formed by pressure being applied to the material to be tableted on a tablet press. A formulation must have good flow properties for precise volumetric feeding of the material to the die cavity and suitable compressibility, compactability, and ejection properties to form a tablet.

There are a number of tablet presses, each varying in productivity but similar in basic function and operation. All compress a tablet formulation within a die cavity by pressure exerted between two steel punches, a lower punch and an upper punch. Tablet presses are typically designed to have a hopper for holding and feeding the formulation, a feeding mechanism for feeding the formulation to the die cavity, provision for placement of punches and dies, and in rotary tablet presses a cam track for guiding the movement of the punches. Two types of tablet presses are the single station or single-punch press and the multistation rotary press. Some tablet presses provide longer dwell times than others, allowing increased bonding to occur. Other presses may provide precompression.

Wet granulation methods may also be employed for preparing the granules of the pharmaceutical composition. Wet granulation methods are described in Remington: The Science and Practice of Pharmacy, Mack Publishing Company, Easton, Pa., 19th Edition 1995. These and other methods are generally known by those skilled in the art. If wet granulation is employed, a volatilizable agent may be incorporated in the mixture before, during or after mixing of the ingredients, but prior to formation of granules. For example, a solid volatilizable agent can be blended with the powders prior to, during or after the addition of binding agent solutions. Other solid dosage forms may be prepared using techniques including rotary bed granulation or spray-dried dispersion (SDD).

The invention will be illustrated in the following non-limiting examples.

EXAMPLES

Example 1

Free Base Plus Succinic Acid

A tablet comprising the free base form of the API (palbociclib) dry granulated with succinic acid was prepared using the following procedure. The tablet had the composition in Table 1.

TABLE 1

| Component | Amount (mg/tablet) |
|---|---|
| Intragranular components | |
| Palbociclib (API) | 125.000 |
| Succinic Acid | 62.500 |
| Microcrystalline cellulose (Avicel PH105) | 62.500 |
| Microcrystalline cellulose (Avicel PH102) | 196.875 |
| Lactose Monohydrate (Fast Flo 316) | 96.875 |
| Crospovidone (Kollidon CL) | 31.250 |
| Colloidal silicon dioxide (Aerosil 200 Pharma) | 6.250 |
| Magnesium Stearate | 6.250 |
| Extragranular components | |
| Crospovidone | 31.250 |
| Magnesium Stearate | 6.25 |
| TOTAL | 625.000 |

Microcrystalline cellulose (Avicel PH105) was added to a blender (bin blender or equivalent) and mixed at low speed for approximately 25 revolutions (2 minutes at 12 rpm). The API was added to the blender, rinsing the API container with a portion of the lactose monohydrate, and folded to mix. The batch quantities of succinic acid, lactose monohydrate, crospovidone, and colloidal silicon dioxide were added to the blender which was mixed at low speed for approximately 180 revolutions (15 minutes at 12 rpm).

A mill and bag were pre-coated with 50% of the batch quantity of microcrystalline cellulose (Avicel PH102). The blend was passed from above through the mill. The mill was flushed with the remaining portion of the microcrystalline cellulose (Avicel PH102), and the milled material transferred from the bag to a blender (bin blender or equivalent) and mixed at low speed for approximately 180 revolutions (15 minutes at 12 rpm). The intragranular magnesium stearate was sieved through an appropriately sized screen and added to the blender from the previous step. The mixture was mixed at low speed for approximately 60 revolutions (5 minutes at 12 rpm). The blend was Roller compacted (Gerteis Minipactor or equivalent), without separating or recycling fines. If in-line milling was not employed, the roller compacted blend was passed through a Comil U5 or U10 equipped with a 1601 impeller, with a screen size of 050G, and a speed of 1000 or 700 rpm, respectively.

The extragranular crospovidone was added to the blender from the previous step. The mixture was mixed at low speed for approximately 180 revolutions (15 minutes at 12 rpm). The extragranular magnesium stearate was sieved through an appropriately sized screen. It was added to the blender from the previous step, and mixed for approximately 60 revolutions (5 minutes at 12 rpm).

To form the tablets, a single station press (Korsch XP 1 or equivalent) or rotary press was used.

Example 2

Bilayer Tablet Formulation

Bilayer tablets containing an active layer and an acid layer were prepared. The active layer consisted of the granulation blend from Example 1.

The active and acid layers had the composition in Table 2.

TABLE 2

| Component | Amount (mg/tablet) |
|---|---|
| Active Layer Granulation | |
| Total according to Example 1 | 625.000 |
| Acid Layer Blend | |
| Tartaric acid, granular | 180.00 |
| Microcrystalline cellulose | 143.100 |
| Crospovidone | 36.00 |
| Magnesium Stearate | 0.900 |
| TOTAL Acid Layer | 360.000 |

The acid layer blend was formed by combining microcrystalline cellulose, tartaric acid and crospovidone into an appropriate sized container. The combination was blended for approximately 120 revolutions, and then passed through a Comil U5 or U10 equipped with a 1601 impeller, with a screen size of 018R and a speed of 1000 rpm or 700 rpm, respectively.

The milled material was transferred to a blender and the components were then blended for approximately 120 revolutions. The magnesium stearate was sieved through an appropriately sized screen (1 mm screen, US Sieve #20) and then added to the blender, and blended for approximately 50 revolutions.

Bilayer tablets were formed using the following procedures using a suitable rotary bilayer tablet press, such as a Korsch XP1. The active layer granulation, (formed according to the procedures outlined in Example 1) was compressed to a target active layer weight of 625 mg and a recommended active layer thickness of 6.66 mm. The acid layer blend was added and the acid layer and active layers compressed to the desired fill weight of 985 mg.

Example 3

Fluid Bed Granulation

The fluid bed coater (a Niro MP-2 Fluid Bed Coater, equipped with a MP-1 bowl, with top spray granulation set-up) was pre-heated using the following conditions until the inlet air dew point (12° C.) and product bowl temperatures stabilized (greater than or equal to 45° C.) to the targets. The spray nozzle was a Schlick 970 with a 0.8 mm liquid tip, and a nozzle to bowl bottom distance of 33 cm.

To form the fluid bed granulation, succinic acid was first milled manually using a mortar and pestle. Periodically, the milled powder was placed on a #60 mesh screen, using manual shaking to pass the material into a collection container. The material retained on the screen was returned to the mortar and more un-milled material was added. Milling was continued until the required amount had passed through the screen.

In addition to succinic acid, each of the following dry bed components in required amounts were individually screened through a #30 mesh into their separate collection containers.

TABLE 3

| Component | Amount (wt %) |
|---|---|
| Microcrystalline cellulose (Avicel PH102) | 37.9 |
| Mannitol | 23.3 |
| Succinic Acid | 30.0 |
| Crospovidone (Polyplasdone XL) | 8.8 |
| TOTAL | 100 |

The binder suspension was formed by adding water to an appropriately sized container. Mannitol and hydroxypropyl cellulose were then added to the container. The solution was mixed for a minimum of 2 hours, and was visually free of agglomerations.

The API was then slowly added to the solution to form the binder suspension. The binder suspension was stirred during processing until it was used. The binder suspension contained the following components in Table 4:

TABLE 4

| Component | Amount (wt %) |
|---|---|
| Palbociclib (API) | 14.24 |
| Mannitol | 2.73 |
| Hydroxypropyl Cellulose (Klucel LF) | 2.73 |
| Water | 80.3 |
| TOTAL | 100.0 |

After the fluid bed product bowl temperature had stabilized, the dry-bed materials were then loaded into the fluid bed in the following order mannitol, microcrystalline cellulose, succinic acid, and crospovidone.

The fluid bed granulation then commenced at a bed temperature of 29-31° C., spray rate of 12-30 g/min, airflow of 70-115 CMH (m$^3$/h) and atomization pressure of 1.1 bar to provide the fluid bed granulation.

Example 4

Fluid Bed Granulation Tablets

Tablets were formed from the fluid bed granulation (FBG) of Example 3, using the following procedures. First, the granulation was dry-sized by passing the granules through a Comil U5 equipped with a 1601 impeller, with a screen size of 018R, and a speed of 1500 rpm. The granules were fed into the Comil as uniformly as possible by visual assessment (20 to 25 minutes for 2 kg granulation). The milled granules were passed through a #60 mesh screen, and the material that passes through the screen was collected in a bag and set aside. Material that was retained on the #60 mesh screen was milled in a Comil a second time. The milled granules were passed through a #60 mesh screen, and the material collected in a bag. Material retained on the #60 mesh screen after the second pass was gently pushed through the screen using a spatula/scraper until all had passed through. The material was added to the bag.

The final tablet blend for the FBG tablets is given in Table 5:

TABLE 5

| Component | Amount (mg/tablet) |
|---|---|
| Intragranular Fluid Bed Granules | |
| FBG according to Example 3 | 400.0 |
| Extragranular Components | |
| Microcrystalline Cellulose (Avicel PH102) | 252.0 |
| Succinic acid | 80.0 |
| Crospovidone (Polyplasdone XL) | 64.0 |
| Magnesium Stearate | 4.0 |
| TOTAL | 800.0 |

An adjusted weight of extragranular components was calculated, if needed, based on the total weight of milled granules from the previous step.

The succinic acid was manually milled (with mortar and pestle) in small aliquots. A sufficient amount was used to ensure the quantity of milled material was sufficient. The milled material was passed through a #60 mesh screen and collected in a new bag. Any material retained on the screen was returned to the mortar with the next aliquot. The required amount of milled succinic acid was subdivided.

Next, the microcrystalline cellulose and crospovidone were passed through a #30 mesh screen and added to a blender. The milled succinic acid and the dry-sized fluid bed granules were added to an appropriate sized blender. The bulk density was 0.39 g/cc. The mixture was blended for 11.25 minutes at 16 rpm (180 revolutions).

Next, the magnesium stearate was combined with 3 to 10 times (volume, estimated visually) of the blend from the previous step in an appropriately sized bottle. The mixture was manually mixed by gently shaking for approximately 30 seconds, and then passing through a 30-mesh screen. The contents were added to the blender and blended for 3.75 minutes at 16 rpm (60 revolutions).

The batch was compressed to the target specifications using a suitable tablet press, such as a Korsch XM12.

Example 5

Spray Dried Dispersion

A solution of hypromellose (HPMC E3 Prem) was prepared by dissolving 3.25 wt % HPMC E3 in a solvent blend of 90/10 methanol/water (w/w) to form a 3.25 wt % HPMC solution. A sufficient quantity of palbociclib (API) was added to this solution to form a spray suspension of the following composition: 1.75 wt % API, 3.25 wt % hypromellose, 85.5 wt % methanol, and 9.5 wt % water. The suspension was then stirred continuously to keep the API from settling in the suspension tank.

The spray dryer was preheated using a heated drying gas (nitrogen) at a flow rate of 1850 g/min and at an inlet drying gas temperature of 130° C. Following preheating, a 90/10 (w/w) methanol/water blend was sprayed until steady-state thermodynamic conditions were achieved. Once the spray dryer reached steady-state, the spray suspension was then introduced into the spray dryer via flash atomization at a feed rate of 130 g/min, at a solution temperature of 130° C., and at a pressure of 250 psi. A secondary nitrogen gas stream was utilized around the nozzle at a pressure of 60 psi to prevent fouling of the nozzle. The particles were collected at a temperature of 45° C. at the outlet of the spray dryer.

After collection, the particles were placed into a convection tray dryer operated at 40° C./15% relative humidity for a minimum of 6 hours. This reduced residual solvent in the particles to no more than 0.3 wt % residual methanol).

The particle sizes of the secondary dried particles were measured by Malvern Particle Size Analyzer, available from Malvern Instruments Ltd. of Framingham, Mass., using low dispersive pressures of 0.5 to 1.0 bar, where D(4,3) is the volume mean diameter; $DV_{10}$ is the diameter that makes up 10% of the total volume containing the particles; $DV_{50}$ is the diameter that makes up 50% of the total volume containing the particles; and $DV_{90}$ is the diameter that makes up 90% of the total volume containing the particles. The particle size is given in Table 6:

TABLE 6

| Particle Size | Diameter (μm) |
| --- | --- |
| D(4, 3) | 11 |
| $DV_{10}$ | 3 |
| $DV_{50}$ | 10 |
| $DV_{90}$ | 22 |

The Span of the particles $(DV_{90}-DV_{10})/DV_{50}$ was 1.96. The bulk specific volume of the particles was 5.6 cc/g, while the tapped specific volume was 3.0 cc/g.

The glass-transition temperature (Tg) of the particles, measured at less than 5% relative humidity was 117.5° C. as measured by Differential Scanning calorimetry (DSC). Powder X Ray diffraction (PXRD) showed the API to be amorphous, with no detectable crystallinity. The particle morphology as measured by scanning electron microscopy (SEM) showed the particles to have whole and collapsed spheres.

Example 6

Comparative Spray Dried Dispersion Tablet

Tablets lacking a water-soluble acid were formed from the spray dried dispersion (SDD) of Example 5 using the following procedure. Half the quantity of microcrystalline cellulose was added to a blender (bin blender or equivalent), and mixed at low speed for approximately 25 revolutions (2 minutes at 12 rpm). The SDD was added to the blender. The blender was rinsed with a portion of sodium chloride and mixed.

Batch quantities of sodium chloride, croscarmellose sodium, and colloidal silicon dioxide were added and mixed at low speed for approximately 180 revolutions (15 minutes at 12 rpm). The final blend is given in Table 7.

TABLE 7

| Component | Amount (mg/tablet) |
| --- | --- |
| Intragranular components | |
| SDD (Example 5) | 357.143 |
| Microcrystalline cellulose (Avicel PH-101) | 191.657 |
| Sodium Chloride | 191.200 |

TABLE 7-continued

| Component | Amount (mg/tablet) |
| --- | --- |
| Croscarmellose Sodium (AC-DI-SOL) | 48.00 |
| Colloidal silicon dioxide (Cab-O-Sil MP5) | 4.00 |
| Magnesium Stearate | 2.00 |
| Extragranular components | |
| Croscarmellose Sodium (AC-DI-SOL) | 32.00 |
| Colloidal Silicon Dioxide (Cab-O-Sil M5P Untreated) | 4.00 |
| Magnesium Stearate | 2.00 |
| TOTAL | 800.00 |

A mill and bag were pre-coated with 25 wt % of the quantity of microcrystalline cellulose. The blend was passed from the above step through the mill, using a Comil U5 equipped with a 1601 impeller, with a screen size of 032R, and a speed of 1000 rpm. The mill was flushed with the remaining batch portion of microcrystalline cellulose, the milled material transferred from the bag to a blender (bin blender or equivalent) and mixed at low speed for approximately 180 revolutions (15 minutes at 12 rpm).

The intragranular magnesium stearate was sieved through an appropriately sized screen and added to the blender from the previous step then mixed at low speed for approximately 60 revolutions (5 minutes at 12 rpm).

The blend was compacted using a Korsch XP 1 or equivalent.

The compacted blend was passed through a mill using a Comil U5 equipped with a 1601 impeller, with a screen size of 050G, and a speed 1000 rpm.

The granulation was transferred from the bag to a blender (bin blender or equivalent). The amount of extragranular colloidal silicon dioxide was calculated and added to the blender from the previous step then mixed for approximately 180 revolutions (15 minutes at 12 rpm). The amount of extragranular magnesium stearate required was calculated, sieved through an appropriately sized screen and added to the blender from the previous step, then mixed for approximately 60 revolutions (5 minutes at 12 rpm).

The tablets were compressed using a single station press (Korsch XP 1 or equivalent).

Example 7

Spray Dried Dispersion Tablet

Tablets were formed from the SDD of Example 5 using the following procedures. Half the quantity of microcrystalline cellulose was added to a blender (bin blender or equivalent), and mixed at low speed for approximately 25 revolutions (2 minutes at 12 rpm). The SDD was added to the blender and the blender was rinsed with a portion of sodium chloride and mixed. The batch quantities of succinic acid, sodium chloride, croscarmellose sodium, and colloidal silicon dioxide were added and mixed at low speed for approximately 180 revolutions (15 minutes at 12 rpm). The final composition of the blend is given in Table 8.

TABLE 8

| Component | Amount (mg/tablet) |
| --- | --- |
| Intragranular components | |
| SDD (Example 5) | 357.143 |
| Microcrystalline cellulose (Avicel PH-101) | 76.457 |
| Succinic Acid | 143.20 |

TABLE 8-continued

| Component | Amount (mg/tablet) |
|---|---|
| Sodium Chloride | 127.20 |
| Croscarmellose Sodium (AC-DI-SOL) | 48.00 |
| Colloidal silicon dioxide (Cab-O-Sil MP5) | 8.00 |
| Magnesium Stearate | 2.00 |
| Extragranular components | |
| Croscarmellose Sodium (AC-DI-SOL) | 32.00 |
| Colloidal Silicon Dioxide (Cab-O-Sil M5P Untreated) | 4.00 |
| Magnesium Stearate | 2.00 |
| TOTAL | 800.00 |

A mill and bag was pre-coated with 25 wt % of the quantity of microcrystalline cellulose. The blend was passed from the above step through the mill, using a Comil U5 equipped with a 1601 impeller, with a screen size of 018R, and a speed of 1000 rpm. The mill was flushed with the remaining batch portion of microcrystalline cellulose, the milled material transferred from the bag to a blender (bin blender or equivalent) and mixed at low speed for approximately 180 revolutions (15 minutes at 12 rpm).

The intragranular magnesium stearate was sieved through an appropriately sized screen and added to the blender from the previous step, then mixed at low speed for approximately 60 revolutions (5 minutes at 12 rpm).

The blend was compacted using a Korsch XP 1 or equivalent.

The compacted blend was passed through a mill using a Comil U5 equipped with a 1601 impeller, with a screen size of 050G, and a speed of 1000 rpm. The amount of extragranular magnesium stearate required was calculated, and sieved through an appropriately sized screen, and added to the blender from the previous step. The mixture was mixed for approximately 60 revolutions (5 minutes at 12 rpm).

The tablets were compressed using a single station press (Korsch XP 1 or equivalent).

Example 8

Dissolution Test 1 at pH 5.5

Test tablet formulations comprising the free base form of palbociclib (API), a water-soluble acid, microcrystalline cellulose (Avicel PH102), lactose monohydrate (Fast Flo 316), crospovidone (Kollidon CL), and magnesium stearate were prepared for dissolution testing. Test tablets were prepared using the dry granulation (DG) method described in Example 1 for the following acids: malic acid, maleic acid, succinic acid, fumaric acid, tartaric acid, tosylic acid, benzoic acid and benzenesulfonic acid. Test tablets were prepared via direct compression (DC) (without dry granulation) for malic acid and citric acid.

The tablets were dissolution tested in a USP 2 apparatus with paddles spinning at 50 rpm, in 500 mL of 10 mM sodium acetate buffer at pH 5.5 and a temperature of 37° C. At each pull point, 6 mL of sample was collected and passed through a 10-μm full-flow filter. Analysis was performed off line at a UV wave length of 367 nm.

Figure 2:
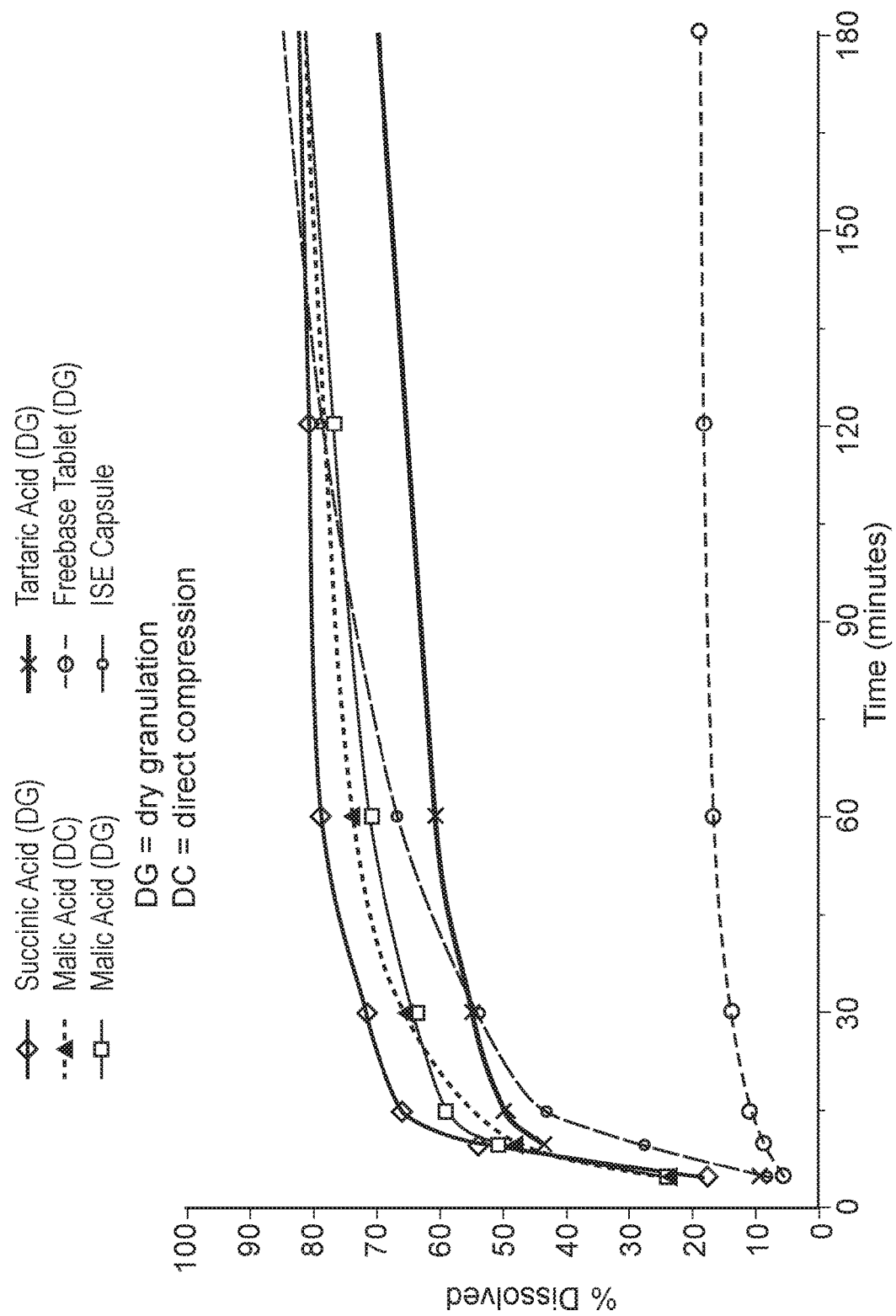
FIG. 2. In vitro dissolution data for prototype formulations comprising succinic acid, malic acid and tartaric acid at 37° C. in a pH 5.5, 10 mM sodium acetate buffer solution in a USP 2 apparatus with paddles spinning at 50 rpm.

Comparative dissolution data were generated for the palbociclib isethionate salt (ISE) capsule and a free base API tablet prepared using the dry granulation method of Example 1, using a blend lacking the water-soluble acid. The results of the dissolution test for tablets comprising succinic acid, maleic acid, malic acid, fumaric acid and tartaric acid are shown in FIG. 1. Tablets comprising succinic acid, malic acid and tartaric acid exhibited superior dissolution performance, with greater than 50% of the drug dissolved at 30 minutes as shown in FIG. 2.

Example 9

Chemical Stability of Formulations

The test tablets prepared in Example 8 were stored at 70° C./75% RH for 8 days. The tablets were crushed and analyzed for impurities using a high-performance liquid chromatography (HLPC) method as follows: Waters CSH C18, 2.1×100 mm, 1.7 μm column; mobile phase (gradient elution) A: 0.03% trifluoroacetic acid, and B: 0.03% trifluoroacetic acid in acetonitrile; column temperature of 45° C.; flow rate of 0.5 mL/min; UV detection at 234 nm; injection volume of 2 μL; and run time of 10.72 minutes. The results are summarized in Table 9.

TABLE 9

| | Storage at 70° C./75% RH for 8 Days | |
|---|---|---|
| Formulation API Free Base plus an Acid | API (Area %) | Total Impurities (Area %) |
| Malic acid | 99.35 | 0.645 |
| Maleic acid | 93.71 | 6.288 |
| Succinic acid | 98.81 | 1.190 |
| Benzoic acid | 99.94 | 0.06 |
| Tosylic acid | 99.46 | 0.54 |
| Tartaric acid | 99.18 | 0.82 |
| Citric acid | 97.18 | 2.82 |
| Benzenesulfonic acid | 99.55 | 0.45 |
| Fumaric acid | 91.94 | 8.06 |

Tablets comprising malic acid, succinic acid, benzoic acid, tosylic acid, tartaric acid and benzenesulfonic acid had acceptable total impurities after storage at 70° C./75% RH for 8 days. On the basis of the superior dissolution and stability experiments, formulations comprising succinic acid, malic acid and tartaric acid were selected for further development.

Example 10

Non-Sink Dissolution Test 2

Figure 3:
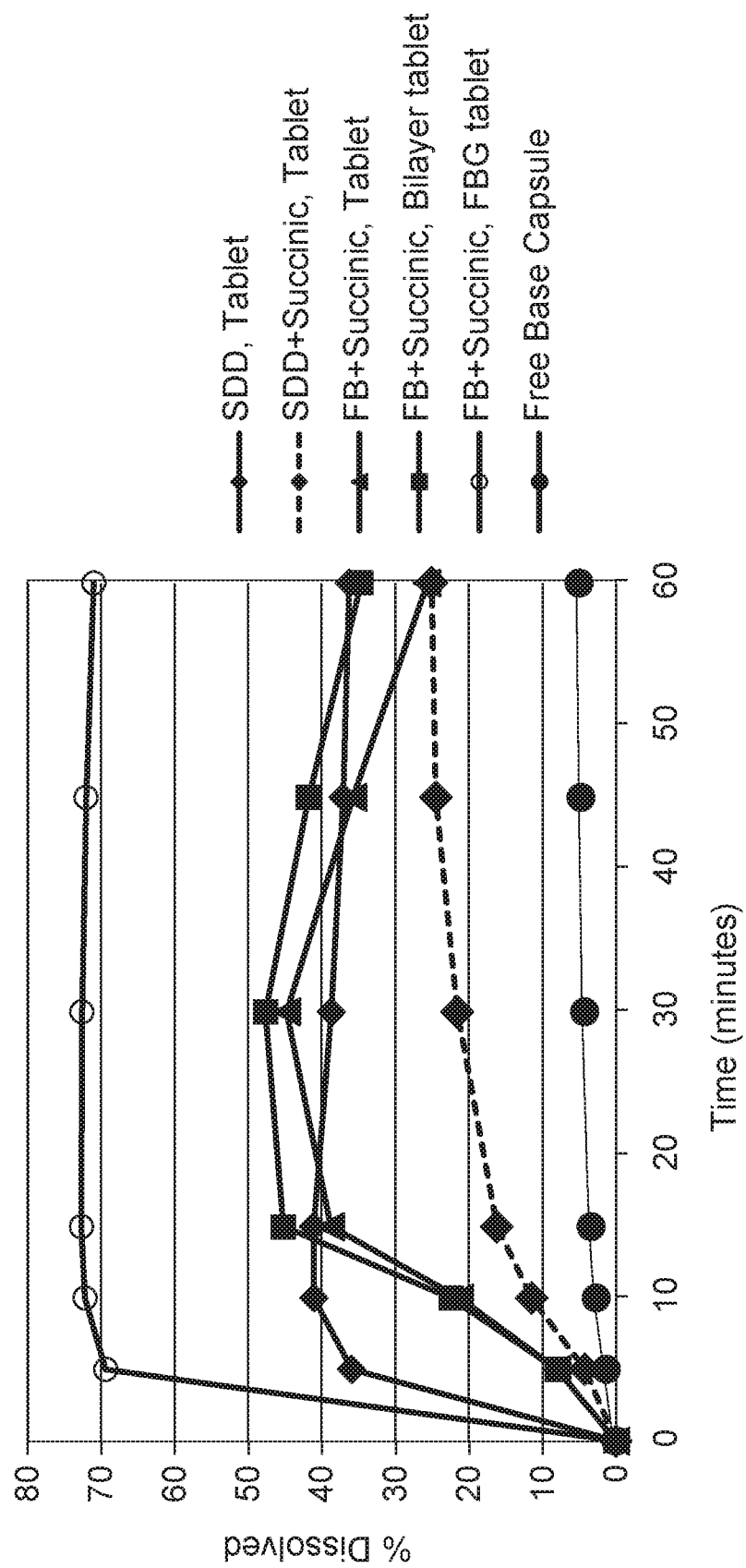
FIG. 3. Non-sink in vitro dissolution data for prototype formulations comprising succinic acid at 37° C. in a pH 6.5, 50 mM phosphate buffer solution containing+0.1 M NaCl, in a USP 2 apparatus with paddles spinning at 50 rpm.

To screen the formulations, a non-sink in vitro dissolution method was developed. In this method, the tablets were placed into USP 2 (paddles) apparatus, with stirring at 50 rpm, and 500 mL of a 50 mM phosphate buffer+0.1 M NaCl (pH 6.5), at a temperature of 37° C. Samples were collected periodically, and filtered through 10-μm filters. The concentration of the API was measured off line at a UV of 367 nm. Dissolution data were generated for the tablets prepared in Example 1 (FB+succinic, tablet), Example 2 (FB+succinic, bi-layer tablet), Example 4 (FB+succinic, FBG tablet), Example 6 (SDD, tablet) and Example 7 (SDD+succinic, tablet). Dissolution profiles are shown in FIG. 3. Also shown is the dissolution data for the commercial free base capsules of palbociclib (free base capsules) having the formulation in Table 10:

TABLE 10

| Component | 125 mg Free base capsule Amount (mg/capsule) |
|---|---|
| Palbociclib (mg) | 125.000 |
| Microcrystalline cellulose (mg) | 185.917 |
| Lactose monohydrate | 92.958 |
| Sodium starch glycolate | 27.000 |
| Colloidal silicon dioxide | 10.125 |
| Magnesium stearate | 9.000 |
| Total fill weight | 450.000 |
| Total capsule weight | 546.000 |

As shown in FIG. 3, subjecting the dosage forms of Examples 1, 2 and 4 to the non-sink dissolution conditions dissolves (a) not less than 40% of the palbociclib in 15 minutes; (b) not less than 35% of the palbociclib in 30 minutes; (c) not less than 25% of the palbociclib in 60 minutes; or (d) two or more of (a),(b) and (c).

Example 11

Drug Exposure Levels with Commercial Free Base Capsules

A randomized, single-dose, open-label, 4-sequence, 4-period cross-over study was run in healthy volunteers. Twenty-eight (28) subjects each received a single dose of palbociclib 125 mg under 4 different conditions or treatments (overnight fasted [A], high-fat meal predose [B], low-fat meal predose [C], and moderate-fat meal 1 hour before and 2 hours post dose [D]).

The treatment sequences used for Periods 1 through 4 are presented in Table 11. There was a washout period of at least 10 days between study periods. Following treatment administration, subjects underwent PK sampling for 144 hours. The pharmacokinetic parameter values are given in Table 12.

TABLE 11

Study Design

| Sequence | Period 1 | Period 2 | Period 3 | Period 4 |
|---|---|---|---|---|
| 1 (n = 7) | A | D | B | C |
| 2 (n = 7) | B | A | C | D |
| 3 (n = 7) | C | B | D | A |
| 4 (n = 7) | D | C | A | B |

TABLE 12

| Parameter (units) | A: Fasted | B: Fed High Fat | C: Fed Low Fat | D: Fed Moderate Fat |
|---|---|---|---|---|
| N | 28 | 28 | 27 | 28 |
| $AUC_{inf}$ (ng-hr/mL) | 1408 | 1672 | 1573 | 1580 |
| $AUC_{last}$ (ng-hr/mL) | 1284 | 1627 | 1524 | 1533 |
| $T_{last}$ (hr) | 119 | 119 | 118 | 119 |
| $C_{last}$ (ng/mL) | 39.22 | 53.67 | 50.20 | 48.64 |
| $T_{max}$ (hr) | 8.00 | 8.00 | 8.00 | 8.00 |
| $T_{1/2}$ (hr) | 23.9 | 22.1 | 22.0 | 22.9 |
| CL/F (L/hr) | 88.77 | 74.74 | 79.45 | 79.10 |
| $V_z/F$ (L) | 2993 | 2342 | 2475 | 2573 |

The palbociclib 125 mg commercial capsule formulation exhibited lower AUC and Cmax when administered under fasted conditions relative to the exposure levels under the three fed conditions. Accordingly, it was recommended that the commercial capsule be administered with food.

Example 12

Effect of Antacid on Bioavailability of Palbociclib

The objective of this study was to investigate the potential effect of increased gastric pH achieved by the treatment of multiple doses of a proton pump inhibitor (PPI, specifically rabeprazole) on the pharmacokinetics (PK) of a single oral 125 mg commercial capsule of palbociclib given under fasted conditions.

The results are summarized in Table 13 below. The palbociclib 125 mg commercial capsule formulation exhibited significantly lower AUC and Cmax when administered in the presence of rabeprazole relative to administration of palbociclib alone.

TABLE 13

| Parameter (units) | Palbociclib Alone | Palbociclib + Rabeprazole |
|---|---|---|
| N, n | 26, 26 | 25, 23 |
| $AUC_{inf}$ (ng-hr/mL) | 1716 (45) | 754.4 (38) |
| $AUC_{last}$ (ng-hr/mL) | 1656 (47) | 672.8 (40) |
| $T_{last}$ (hr) | 120 (72.0-120) | 96.0 (72.0-120) |
| $C_{max}$ (ng/mL) | 49.31 (72) | 12.25 (44) |
| $T_{max}$ (hr) | 7.00 (6.00-24.0) | 24.0 (6.00-48.0) |
| $T_{1/2}$ (hr) | 21.97 ± 2.9721 | 22.45 ± 4.2139 |
| CL/F (L/hr) | 72.85 (45) | 165.7 (38) |
| $V_z/F$ (L) | 2290 (49) | 5289 (31) |

Example 13

Effect of Antacid on Bioavailability of Test Formulations

A crossover, open label, non-randomized, pharmacokinetic study in healthy volunteers was conducted to estimate the effect of antacid treatment on the bioavailability of a 125 mg tablet (single dose) of six experimental formulations of palbociclib in the presence of rabeprazole relative to administration of palbociclib alone under fasted conditions. Table 14(A)-(F) shows the results for Cohorts 1-6, Example 1; Example 6; Example 7; Example 2; Example 4; and 125 mg palbociclib oral solution, respectively.

TABLE 14

| Plasma Palbociclib Parameters [Units] | Adjusted Geometric Means | | Ratios | |
|---|---|---|---|---|
| | Palbociclib + Rabeprazole (Test) | Palbociclib Alone (Reference) | (Test/Reference) of Adjusted Means | 90% CIs for Ratios |
| (A) Summary results for Cohort 1 (tablets of Example 1). | | | | |
| AUCinf [ng · hr/mL] | 1458 | 1449 | 100.61 | (95.25, 106.27) |
| Cmax [ng/mL] | 45.91 | 49.25 | 93.22 | (81.71, 106.35) |
| (B) Summary results for Cohort 2 (tablets of Example 6). | | | | |
| AUCinf [ng · hr/mL] | 1079 | 1120 | 96.31 | (90.78, 102.18) |
| Cmax [ng/mL] | 36.54 | 39.86 | 91.68 | (80.91, 103.88) |
| (C) Summary results for Cohort 3 (tablets of Example 7). | | | | |
| AUCinf [ng · hr/mL] | 1548 | 1495 | 103.6 | (94.39, 113.70) |
| Cmax [ng/mL] | 46.83 | 48.21 | 97.13 | (84.41, 111.78) |
| (D) Summary results for Cohort 4 (tablets of Example 2) | | | | |
| AUCinf [ng · hr/mL] | 1443 | 1418 | 101.78 | (94.95, 109.09) |
| Cmax [ng/mL] | 45.18 | 47.50 | 95.12 | (87.03, 103.96) |
| (E) Summary results for Cohort 5 (tablets of Example 4) | | | | |
| AUCinf [ng · hr/mL] | 1962 | 1803 | 108.83 | (103.64, 114.28) |
| Cmax [ng/mL] | 64.91 | 62.52 | 103.83 | (94.55, 114.02) |
| (F) Summary results for Cohort 6 (Oral solution) | | | | |
| AUCinf [ng · hr/mL] | 1478 | 1451 | 101.83 | (93.67, 110.69) |
| Cmax [ng/mL] | 47.77 | 50.24 | 95.07 | (85.18, 106.11) |

Example 14

Accelerated Stability Tests

The tablets of Example 1 (dry granulation+succinic acid) were placed on accelerated stability using the following conditions. Tablets were place into beakers at the conditions listed below. Humidity control was achieved either through oven control or saturated salt solutions. Samples were removed from the conditions periodically as shown in Table 15 below. Samples (including unexposed controls) were stored in a refrigerator until analysis.

The following saturated salt solutions maintained the designated relative humidity: 22% RH controlled via potassium acetate; 50% RH controlled via sodium bromide for the 30° and 40° C. conditions; and 75% RH via humidity controlled ovens.

TABLE 15

| Temperature (° C.) | Relative Humidity (%) | Time (days) | Degradant* (wt %) |
|---|---|---|---|
| 0 | 0 | 0 (initial) | 0 (initial) |
| 30 | 22 | 96 | 0.05 |
| 30 | 50 | 96 | 0.07 |
| 30 | 75 | 96 | 0.12 |

The degradant is the succinyl adduct of the API, having the structure:

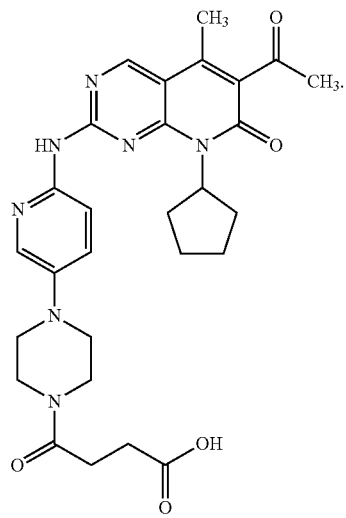 [SMILES: CC(=O)c1c(C)c2cnc(Nc3ccc(N4CCN(C(=O)CCC(=O)O)CC4)cn3)nc2n(C2CCCC2)c1=O]

Samples were prepared by adding each tablet to a 100 mL volumetric flask, adding a stir bar and approximately 100 mL of the dissolving solvent (1440 mL water:400 mL acetonitrile:160 mL 1N HCl; 0.1 N HCl: acetonitrile 80:20). The flask was placed on a stir plate and sample was stirred for one hour at the highest useable stir speed. An aliquot was then removed and centrifuged in a polypropylene tube at 3000 RPM for 5 minutes. The supernatant was diluted 1:5 with dissolving solvent and sampled into an HPLC vial for analysis. Each tablet contained 125 mg API for a final solution concentration of 0.25 mg/mL. The samples were analyzed using the HPLC method below. The results are presented in Table 15 above, and show excellent long-term stability.

Dissolving Solvent (Diluent):
1440 mL water: 400 mL acetonitrile: 160 mL 1N HCl /// (0.1 N HCl: acetonitrile 80:20)

Mobile Phase:
Mobile Phase A: 0.03% trifluoroacetic acid (0.6 mL of trifluoroacetic acid into 2000 mL of water)
Mobile Phase B: 0.03% trifluoroacetic acid in acetonitrile (0.6 mL of trifluoroacetic acid into 2000 mL of acetonitrile)
0.5 mL/min
Gradient

| | | |
|---|---|---|
| Initial | 88% A | 12% B |
| 0.22 min | 88% A | 12% B |
| 8.72 min | 15% A | 85% B |
| 8.82 min | 88% A | 12% B |
| 10.72 min | Total run time | |

234 nm, area % vs palbociclib (main band)
2 µL injection of samples (prepared as directed below).
Sample chamber maintained at 5° C.

Sample Preparation

Samples were prepared by adding each tablet to a 100 mL volumetric flask, adding a stir bar and approximately 100 mL of the dissolving solvent. The flask was placed on a stir plate and sample was stirred for one hour at the highest useable stir speed. An aliquot was then removed and centrifuged in a polypropylene tube at 3000 RPM for 5 minutes. The supernatant was diluted 1:5 with dissolving solvent and sampled into an HPLC vial for analysis. Each tablet contained 125 mg palbociclib for a final solution concentration of 0.25 mg/mL.

In addition, the tablets of Example 4 (fluid bed granulation+succinic acid) were analyzed in the same manner. The results are presented in the following Table 16, and show that the degradant concentration was unacceptable for long-term stability.

TABLE 16

| Temperature (° C.) | Relative Humidity (%) | Time (days) | Degradant* (wt %) |
|---|---|---|---|
| 0 | 0 | 0 (initial) | 0 (initial) |
| 30 | 22 | 96 | 0.211 |
| 30 | 50 | 96 | 0.263 |
| 30 | 75 | 96 | 0.444 |

*The degradant is the succinyl adduct of the API

Example 15

Long Term Storage Stability

The tablets of Example 1 were packaged with a desiccant canister in a bottle using a heat-induction seal. After storage for 1 year at 25° C./60% RH, the tablets had a succinyl adduct level of less than 0.05%. The tablets of Example 4 were packaged with a desiccant canister in a HDPE bottle using a heat-induction seal. After storage for 6 months at 25° C./60% RH, the tablets had a succinyl adduct level of 0.23%.

Example 16

Film Coated Tablet Formulations

Table 17 describes optimized Formulations A1, A2 and B, which showed acceptable manufacturing performance for solid dosage form commercialization. The tablets were formed using the following procedure. The microcrystalline cellulose PH102, colloidal silicon dioxide, intragranular crospovidone CL, and API were blended together and passed through a Comil for homogenization. Intragranular magnesium stearate was blended in. The mixture was dry granulated using roller compaction and granule milling.

Sieved succinic acid, microcrystalline cellulose PH-200, and extragranular crospovidone (CL or CL-SF grade) were blended into the granules. Extragranular magnesium stearate or sodium stearyl fumarate was mixed into the final blend as a tableting lubricant. Tablets were formed using a rotary tablet press with pre-compression. Formulation A2 used an external lubrication system (ELS) to apply a nominal amount of lubricant directly to the tablet punch tips.

Tablets were film coated to a weight gain of 2 to 4% using Opadry Pink (03K140024) and purified water to a solids content of 12% w/w.

TABLE 17

Optimized formulations

| | Quantity/unit: (mg/tablet) | | |
|---|---|---|---|
| Component: | Formulation A2 | Formulation A1 | Formulation B |
| Intragranular Components | | | |
| Palbociclib (API) | | 125.000 | |
| Microcrystalline Cellulose (Avicel PH102) | | 244.812 | |
| Colloidal Silicon Dioxide (Aerosil 200 Pharma) | | 6.250 | |
| Crospovidone (Kollidon CL) | | 18.750 | |
| Magnesium Stearate | | 2.063 | |
| Extragranular Components | | | |
| Succinic Acid extra pure, (100 to 350 micron) | | 62.500 | |
| Microcrystalline Cellulose (Avicel PH-200) | 143.750 | 134.375 | 115.625 |
| Crospovidone (Kollidon CL or CL-SF) | 18.750 (CL) | 18.750 (CL-SF) | |
| Sodium Stearyl Fumarate (PRUV) | — | | 31.250 |
| Magnesium Stearate (standard or fine grade) | 3.125 (standard) | 12.500 (fine) | — |
| Tablet Core | | 625.000 | |
| Opadry Pink (03K140024) | | 18.750 | |
| Purified Water (removed during final processing) | | (137.500) | |
| Final Coated Tablet | | 643.750 | |

Example 17

Optimization of Lubricant Level

Formulations were prepared as described for Formulation A2 in Example 16 with different levels of intragranular and extragranular magnesium stearate lubricant, as shown in Table 17. Hardness (tablet breaking force, USP <1217>), friability (USP <1216> for 100 revolutions), extended friability (USP <1216> for 375 revolutions), and punch sticking (Hutchins, MacDonald, Mullarney, Assessing Tablet-Sticking Propensity, Pharmaceutical Technology, Volume 36, Issue 1, 2012) were measured for each formulation as reported in Table 18. Reduced sample sizes were used for the USP methods.

Reducing both the intragranular and extragranular lubricant levels significantly increased tablet hardness and reduced friability. Tablet sticking was more sensitive to extragranular lubricant level than intragranular lubricant level. Sticking was significantly reduced by increasing extragranular magnesium stearate level. No difference in knurled/smooth roller sticking was observed with different intragranular magnesium stearate levels. As shown in Table 18, reducing the intragranular/ extragranular lubricant ration from 1 wt %/0 wt % to 0.33 wt %/0.5 wt % provided with good tablet strength, reduced friability, and reduced sticking for tablets of Formulation A2. Lubricant levels of about 5 wt % sodium stearyl fumarate or 2 wt % fine grade stearate (CaSt 2249) alleviated punch sticking and tablet defects.

TABLE 18

Optimization of lubricant level.

| Intragranular Lubricant Level (%) | Extragranular Lubricant Level (%) | Hardness (kP) | Friability (%) | Extended friability (%) | Sticking (ug) |
|---|---|---|---|---|---|
| 0.33 | 0 | 22 | 0.08 | 0.23 | 2914 |
|  | 0.5 | 19 | 0.09 | 0.28 | 766 |
|  | 1 | 16 | 0.15 | 0.54 | 304 |
| 0.67 | 0 | 21 | 0.13 | 0.45 | 1977 |
|  | 0.5 | 18 | 0.13 | 0.38 | 563 |
|  | 1 | 16 | 0.11 | 0.49 | 142 |
| 1 | 0 | 18 | 0.00 | 0.36 | 1346 |
|  | 0.5 | 18 | 0.09 | 0.43 | 428 |
|  | 1 | 15 | 0.14 | 0.57 | 242 |

Example 18

Optimization of Tablet Hardness and Friability

Formulations were prepared as generally described for Formulation A2 in Example 16, with changes to the order of addition of acid, addition of lactose monohydrate, addition of dry binders (Kollidon SF, Avicel PH105, Klucel EXF), and change in the intragranular to extragranular ratio of microcrystalline cellulose. The properties of these different formulations were measured: initial blend bulk density (USP <616>), roller compacted ribbon tensile strength (Zinchuk A V, Mullarney M P, Hancock B C. Simulation of roller compaction using a laboratory scale compaction simulator. Int J Pharm. 2004 Jan. 28; 269(2):403-15.), punch sticking (Hutchins, MacDonald, Mullarney, Assessing Tablet-Sticking Propensity, Pharmaceutical Technology, Volume 36, Issue 1, 2012), tablet hardness (tablet breaking force, USP <1217>), friability (USP <1216> for 375 revolutions), and disintegration time (USP <701>). Reduced sample sizes were used for the USP methods.

Formulations without lactose showed higher tablet hardness and lower friability. Additionally, adding the SF (superfine) grade of Kollidon helped decrease disintegration time while increasing tablet hardness. Adding the acid extragranularly was found to be preferable to obtain shorter disintegration times.

Removal of lactose from the formulation provided tablets having reduced friability which maintained rapid disintegration. The inclusion of dry binders did not provide additional benefit to reducing friability, but marginally reduced sticking. However, the inclusion of binders can in some cases negatively impact disintegration/swelling.

TABLE 19

Optimization of diluent and binder components

| Example | Initial blend bulk density (g/cc) | Ribbon Tensile Strength (MPa) | Sticking (ug) | Hardness (kp) | Friability (%) | Disint. Time (m:s) |
|---|---|---|---|---|---|---|
| Control (incl. lactose) | 0.33 | 1.4 | 1074 | 16 | 0.44 | 1:51 |
| Remove lactose | 0.31 | 1.8 | 1029 | 20 | 0.27 | 2:41 |
| Move Acid from EG to IG (incl. lactose) | 0.40 | 1.0 | N/A | 19 | 0.21 | 8:15 |
| Add Kollidon SF (no lactose) | 0.24 | 3.1 | 728 | 22 | 0.37 | 1:20 |
| Add Avicel PH105 (no lactose) | 0.31 | 2.1 | 975 | 19 | 0.47 | 2:26 |
| Add Klucel EXF (no lactose) | 0.31 | 1.5 | 842 | 18 | 0.25 | 50:41 |
| Move EG Avicel to IG (no lactose) | 0.33 | 2.8 | 1392 | 18 | 0.28 | 03:30 |

Example 19

In Vitro Dissolution of Formulations A1, A2 and B

Figure 4:
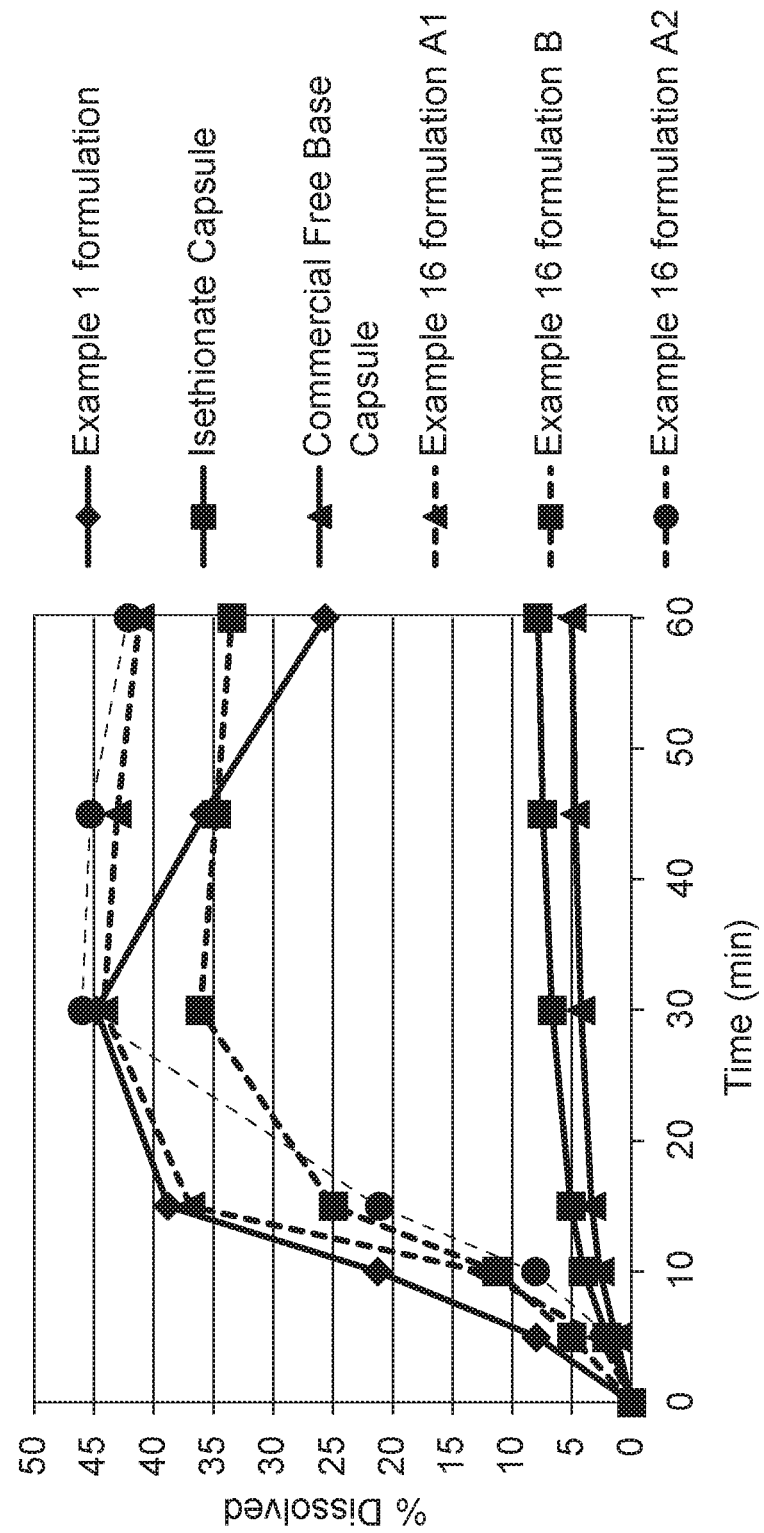
FIG. 4. Non-sink in vitro dissolution data for formulations A1, A2 and B at 37° C. in a pH 6.5, 50 mM phosphate buffer solution containing+0.1 M NaCl, in a USP 2 apparatus with paddles spinning at 50 rpm.

In vitro dissolution of optimized formulations A1, A2 and B was determined using Dissolution Test 2, under the non-sink conditions (pH 6.5, 50 mM phosphate buffer, 0.1 M NaCl) described in Example 10. The dissolution profiles of these formulations were compared to the tablets prepared according to Examples 1-7. The tablet of Example 1 showed no drug-drug interaction with a proton pump inhibitor in the fasted state in human volunteers and was set as the minimum target dissolution profile. Comparative dissolution data are presented in FIG. 4. Formulations A1, A2 and B were all superior to both the commercial free base capsules (prepared as described in Example 10) and the palbociclib isethionate salt (ISE) capsules used in early development having the formulation in Table 20. After 10 minutes, the formulations A1, A2 and B were all superior to the tablets of Examples 1-7, and therefore met the solid dosage form dissolution target.

TABLE 20

| Component | 25 mg ISE capsule Amount (mg/capsule) | 100 mg ISE capsule Amount (mg/capsule) |
|---|---|---|
| Palbociclib isethionate (mg) | 32.048 (eq. 25 mg FB) | 128.200 (eq. 100 mg FB) |
| Microcrystalline cellulose (mg) | 102.802 | 148.500 |
| Sodium starch glycolate | 8.700 | 13.500 |

TABLE 20-continued

| Component | 25 mg ISE capsule Amount (mg/capsule) | 100 mg ISE capsule Amount (mg/capsule) |
|---|---|---|
| Magnesium stearate | 1.450 | 2.300 |
| Corn starch | 145.000 | 157.500 |
| Total fill weight | 290.00 | 450.000 |

Example 20

Impact of Succinic Acid Particle Size Distribution

The impact of succinic acid particle size distribution on the rate of formation of the succinyl adduct was assessed for as-received acid (broad particle size distribution up to 1 mm diameter) and three sieve cuts of the acid. Smaller acid particle size resulted in a greater rate of impurity formation because of its larger specific surface area enabling a higher frequency of contacts of the acid with the free base API. Therefore acid with a particle size greater than approximately 100 microns was preferred in the drug product formulation to improve chemical stability.

TABLE 21

Impact of succinic acid particle size distribution on adduct formation

| Storage Condition (° C./% RH) | Acid degradation rate (%/year) | | | |
|---|---|---|---|---|
| | As-received acid, without sieving | Acid sieved to <106 μm | Acid sieved to 150-250 μm | Acid sieved to 425-600 μm |
| 25° C./22% RH | 0.092 | 0.150 | 0.071 | 0.035 |
| 25° C./60% RH | 0.253 | 0.346 | 0.167 | 0.082 |
| 30° C./22% RH | 0.203 | 0.294 | 0.150 | 0.075 |
| 30° C./75% RH | 0.837 | 0.942 | 0.494 | 0.249 |

Example 21

Physical Stability Analysis

A quantitative Raman spectroscopic method was developed to evaluate the physical stability of the formulations. The Raman method uses a Kaiser Optical Systems PhAT probe and the quantitation model was built utilizing a set of calibration standards prepared from API, API succinate complex and excipients. The relative stability of Formulations A1 and B were assessed by determining the amount of API succinate complex in the formulation after storing the tablets at 30 to 50° C. and up to 75% RH for up to 1 month.

Formulation B showed lower conversion to the succinate complex relative to Formulation A1. The amount of conversion increased over time and was accelerated by storage conditions with higher temperature and humidity.

The amount of API succinate complex formed under various temperature and humidity conditions for formulation A1 and B is shown in Table 22 as a function of time, where "LOD" refers to the limit of detection and "LOQ" refers to the limit of quantification.

TABLE 22

Conversion of free base API to API succinate complex

| Storage Condition (° C./% RH) | 2 weeks Formulation A1 | 2 weeks Formulation B | 1 month Formulation A1 | 1 month Formulation B |
|---|---|---|---|---|
| Initial | <2% (LOD) | <2% (LOD) | <2% (LOD) | <2% (LOD) |
| 50/75 | 56% | 32% | — | — |
| 50/low | <5% (LOQ) | <5% (LOQ) | — | — |
| 40/75 | — | — | 56% | 33% |
| 30/75 | — | — | 13% | 10% |

The physical stability of prototype non-coated tablet formulation A1 under open conditions was assessed. Tablets were subjected to elevated temperatures and humidity. Conversion to the succinate complex was observed in stressed samples using Raman spectroscopy.

The chemical purity of Formulations A1 and B were compared after storage for 1 month at 40° C./75% RH. As shown in Table 23, Formulation B showed a significantly lower extent of total impurity formation relative to Formulation A1.

TABLE 23

Degradation of Formulations A1 and B after 1 month at 40 C./75% RH

| Impurity | Formulation A1 % Impurity | Formulation B % Impurity |
|---|---|---|
| Oxidative degradant 1 | 0.15% | NMT |
| Oxidative degradant 2 | 0.19% | 0.05% |
| Fumarate adduct | ND | 0.15% |
| Oxidative degradant 3 | 0.35% | 0.07% |
| Unidentified degradant | 0.13% | ND |
| Oxidative degradant 4 | 0.38% | 0.08% |
| Succinyl adduct | 0.18% | 0.18% |
| Oxidative degradant 5 | 0.21% | NMT |
| Formyl adduct | 0.45% | 0.15% |
| Total Impurity | 2.1% | 0.75% |

Based on these data, humidity (% RH) was determined to have a significant impact on the rate of API conversion from free-base to succinate complex. Increasing temperature also impacted conversion to the complex, but had a weaker effect than humidity.

Tablets which were pre-equilibrated in 60% RH before foil-foil packaging displayed rapid succinate complex formation. The 9 week stability data indicated that control of water activity in tablets was required to minimize formation of the palbociclib succinate complex in the drug product. Formulation B (which contains extragranular sodium stearyl fumarate as the lubricant) showed less succinate complex conversion in comparison to formulation A1 (which incorporates magnesium stearate as the extragranular lubricant) under conditions of high humidity (75% RH).

We claim:

1. A tablet consisting of about 20 wt % of palbociclib, about 10 wt % of succinic acid, about 50 wt % to about 75 wt % of microcrystalline cellulose, about 5 wt % to about 10 wt % of crospovidone, about 0.5 wt % to about 6 wt % of magnesium stearate, and about 0.5 wt % to about 2 wt % of silicon dioxide.

2. The tablet of claim 1, wherein the tablet is film coated.

3. The tablet of claim 1, wherein the amount of palbociclib in the tablet is 25 mg, 75 mg, 100 mg or 125 mg.

4. The tablet of claim 3, wherein the amount of palbociclib in the tablet is 125 mg.

5. A tablet consisting of: (i) as intragranular components, about 20 wt % of palbociclib, about 39.2 wt % of microcrystalline cellulose, about 1 wt % of silicon dioxide, about 3 wt % of crospovidone, and about 0.3 wt % of magnesium stearate; and (ii) as extragranular components, about 10 wt % of succinic acid, about 21.5 wt % of microcrystalline cellulose, about 3 wt % of crospovidone, and about 2 wt % of magnesium stearate.

6. The tablet of claim 5, comprising 25.0 mg, 75.0 mg, 100.0 mg or 125.0 mg of palbociclib.

7. The tablet of claim 6, wherein the tablet is film coated to a weight gain of about 2% to about 4%.

8. A tablet consisting of:
(i) intragranular components:

| | |
|---|---|
| palbociclib | 125.000 mg |
| microcrystalline cellulose (Avicel PH102) | 244.812 mg |
| colloidal silicon dioxide (Aerosil 200 Pharma) | 6.250 mg |
| crospovidone (Kollidon CL) | 18.750 mg |
| magnesium stearate | 2.063 mg | and
(ii) extragranular components:

| | |
|---|---|
| succinic acid (100 to 350 micron) | 62.500 mg |
| microcrystalline Cellulose (Avicel PH200) | 134.375 mg |
| crospovidone (Kollidon CL-SF) | 18.750 mg |
| magnesium stearate (fine grade) | 12.500 mg. |

9. The tablet of claim 8, wherein the tablet is film coated to a weight gain of 4% with a film coating.

* * * * *